(12) United States Patent
Mandelis et al.

(10) Patent No.: US 9,810,650 B2
(45) Date of Patent: Nov. 7, 2017

(54) SYSTEMS AND METHODS FOR PERFORMING TRUNCATED-CORRELATION PHOTOTHERMAL COHERENCE TOMOGRAPHY

(71) Applicants: Andreas Mandelis, Scarborough (CA); Sreekumar Kaiplavil, Sutton (GB)

(72) Inventors: Andreas Mandelis, Scarborough (CA); Sreekumar Kaiplavil, Sutton (GB)

(*) Notice: Subject to any disclaimer, the term of this patent is extended or adjusted under 35 U.S.C. 154(b) by 236 days.

(21) Appl. No.: 14/518,984

(22) Filed: Oct. 20, 2014

(65) Prior Publication Data
US 2016/0109393 A1    Apr. 21, 2016

(51) Int. Cl.
*G01J 5/02* (2006.01)
*G01N 25/72* (2006.01)
(Continued)

(52) U.S. Cl.
CPC ............... *G01N 25/72* (2013.01); *G01J 5/10* (2013.01); *G01N 29/0672* (2013.01);
(Continued)

(58) Field of Classification Search
CPC ........ G01N 25/72; G01N 29/0672; G01J 5/10
(Continued)

(56) References Cited

U.S. PATENT DOCUMENTS 5,667,300 A  9/1997 Mandelis et al.
6,584,341 B1 6/2003 Mandelis et al.
(Continued)

FOREIGN PATENT DOCUMENTS

WO    2014094142    6/2014

OTHER PUBLICATIONS

Kaiplavil et al. (Jul. 7, 2014), "Photothermal tomography for the functional and structural evaluation, and early mineral loss monitoring in bones", Biomedical Optics Express, 5(8) pp. 2488-2502.*
(Continued)

*Primary Examiner* — David Porta
*Assistant Examiner* — Abra Fein
(74) *Attorney, Agent, or Firm* — Hill & Schumacher

(57) ABSTRACT

Photothermal imaging systems and methods are disclosed that employ truncated-correlation photothermal coherence tomography (TC-PCT). According to the example methods disclosed herein, photothermal radiation is detected with an infrared camera while exciting a sample with the chirped delivery of incident laser pulses (where the pulses have a fixed width), and time-dependent photothermal signal data is obtained from the infrared camera and processed using a time-evolving filtering method employing cross-correlation truncation. The cross-correlation truncation method results in pulse-compression-linewidth-limited depth-resolved images with axial and lateral resolution well beyond the well-known thermal-diffusion-length-limited, depth-integrated nature of conventional thermographic and thermo-photonic modalities. As a consequence, an axially resolved layer-by-layer photothermal image sequence can be obtained, capable of reconstructing three-dimensional visualizations (tomograms) of photothermal features in wide classes of materials. Additional embodiments are disclosed in which the aforementioned systems and methods are adapted to photo-acoustic and acousto-thermal imaging.

19 Claims, 23 Drawing Sheets
(19 of 23 Drawing Sheet(s) Filed in Color)

(51) Int. Cl.
   *G01J 5/10* (2006.01)
   *G01N 29/06* (2006.01)
   *G01N 29/24* (2006.01)
   *G01N 29/34* (2006.01)
   *G01J 5/00* (2006.01)

(52) U.S. Cl.
   CPC ....... *G01N 29/2418* (2013.01); *G01N 29/343* (2013.01); *G01J 2005/0077* (2013.01)

(58) Field of Classification Search
   USPC ...................................................... 250/341.6
   See application file for complete search history.

(56) References Cited

U.S. PATENT DOCUMENTS

| | | |
|---|---|---|
| 7,045,786 B2 | 5/2006 | Mandelis et al. |
| 7,116,421 B2 | 10/2006 | Garcia et al. |
| 7,525,661 B2 | 4/2009 | Mandelis et al. |
| 7,729,734 B2 | 6/2010 | Mandelis et al. |
| 8,306,608 B2 | 11/2012 | Mandelis et al. |
| 8,649,835 B2 | 2/2014 | Mandelis et al. |
| 2002/0011852 A1 | 1/2002 | Mandelis et al. |
| 2005/0131289 A1* | 6/2005 | Aharoni ............. A61B 5/02007 600/407 |
| 2006/0253020 A1* | 11/2006 | Ehman ............. G01R 33/56358 600/411 |
| 2012/0308120 A1* | 12/2012 | Placko ................ G01N 27/9046 382/154 |
| 2013/0102865 A1 | 4/2013 | Mandelis et al. |
| 2013/0141558 A1 | 6/2013 | Jeon et al. |
| 2013/0278749 A1 | 10/2013 | Mandelis et al. |
| 2014/0085449 A1* | 3/2014 | Mandelis ............. A61B 5/0073 348/77 |
| 2014/0200456 A1* | 7/2014 | Owen .................. A61B 8/4427 600/447 |

OTHER PUBLICATIONS

Kaiplavil et al. (Feb. 2014), "Truncated-correlation photothermal coherence tomography of artificially demineralized animal bones: two- and three-dimensional markers for mineral loss monitoring", Journal of Biomedical Optics, 19(2), pp. 1-14.*

Kaiplavil, S., & Mandelis, A. (2011). "Highly Depth-Resolved Chirped Pulse Photothermal Radar for Bone Diagnostics". Review of Scientific Instruments, 82, 074906.

* cited by examiner

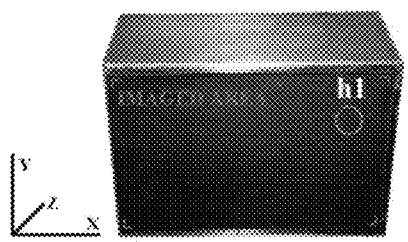 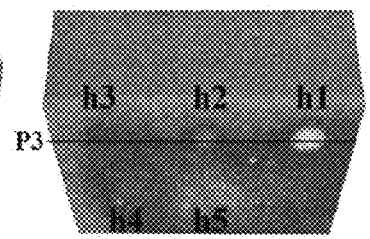 
FIG. 5A    FIG. 5B    FIG. 5C
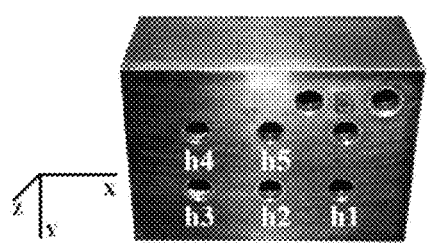 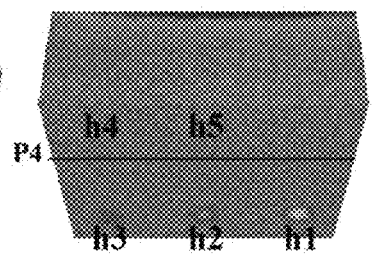 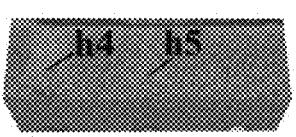
FIG. 5D    FIG. 5E    FIG. 5F
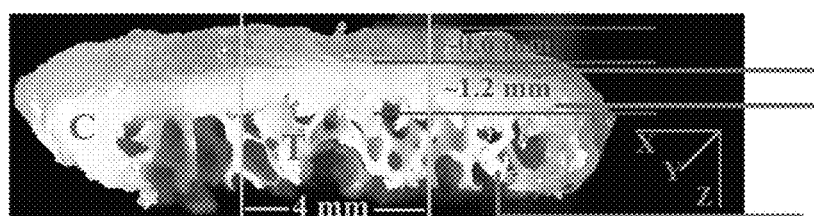 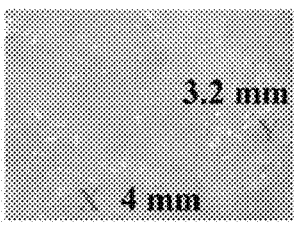
FIG. 6A    FIG. 6B
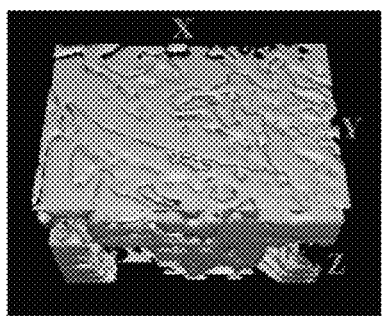 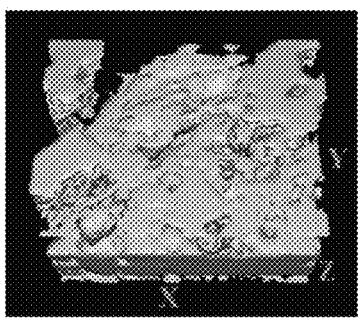 
FIG. 6C    FIG. 6D    FIG. 6E

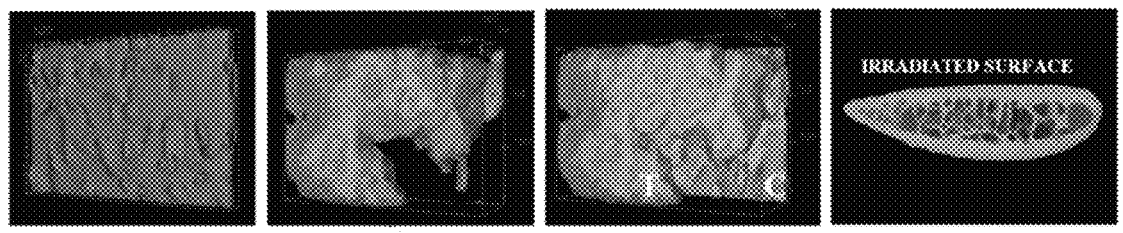
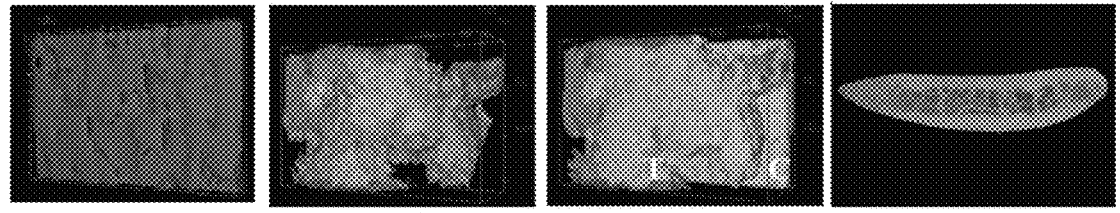
FIG. 7A  FIG. 7B  FIG. 7C  FIG. 7D
FIG. 7E  FIG. 7F  FIG. 7G  FIG. 7H

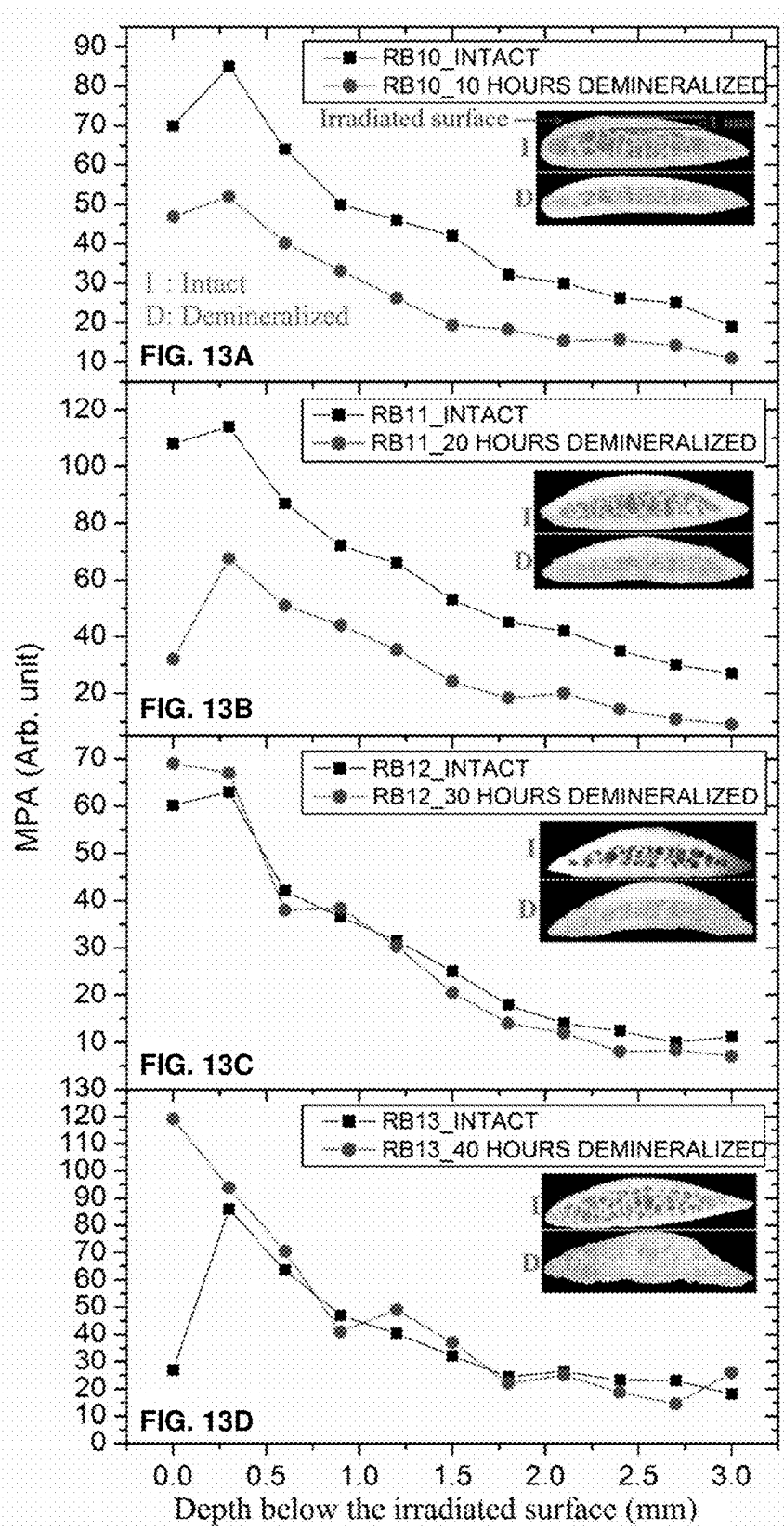

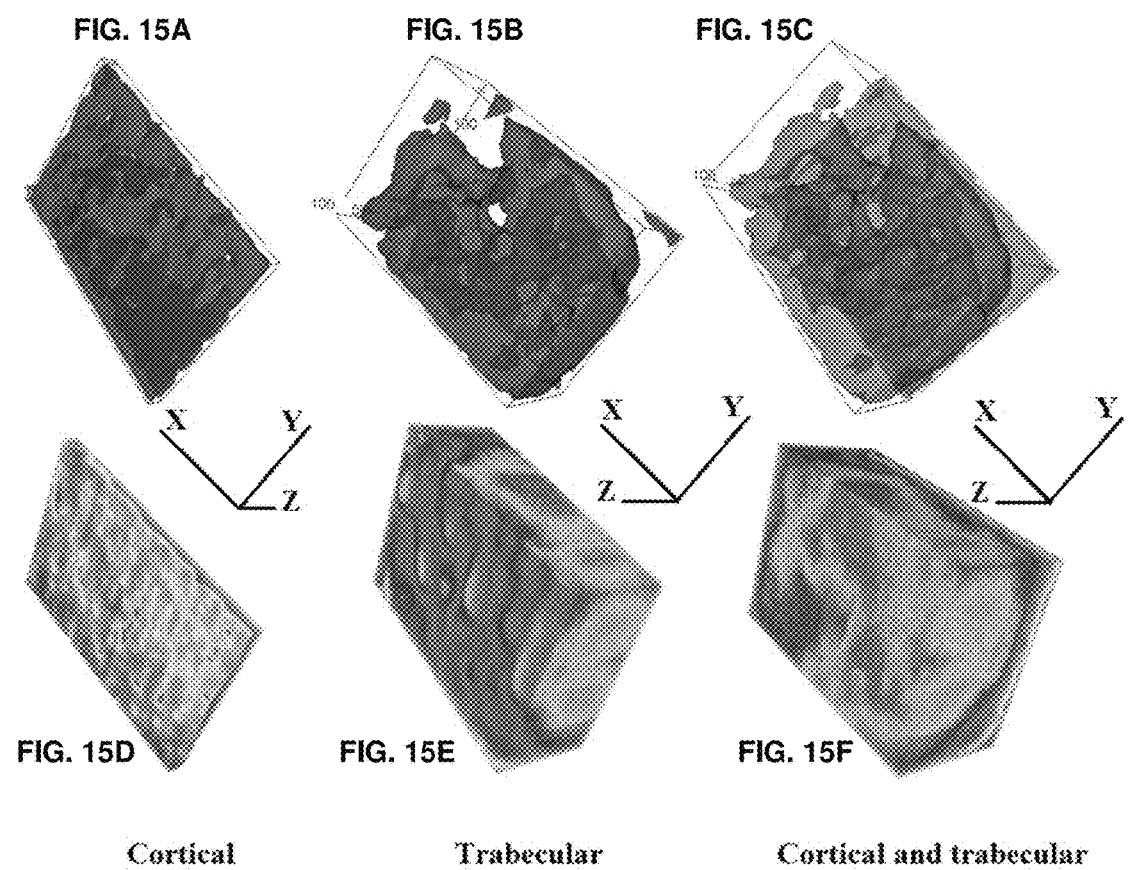

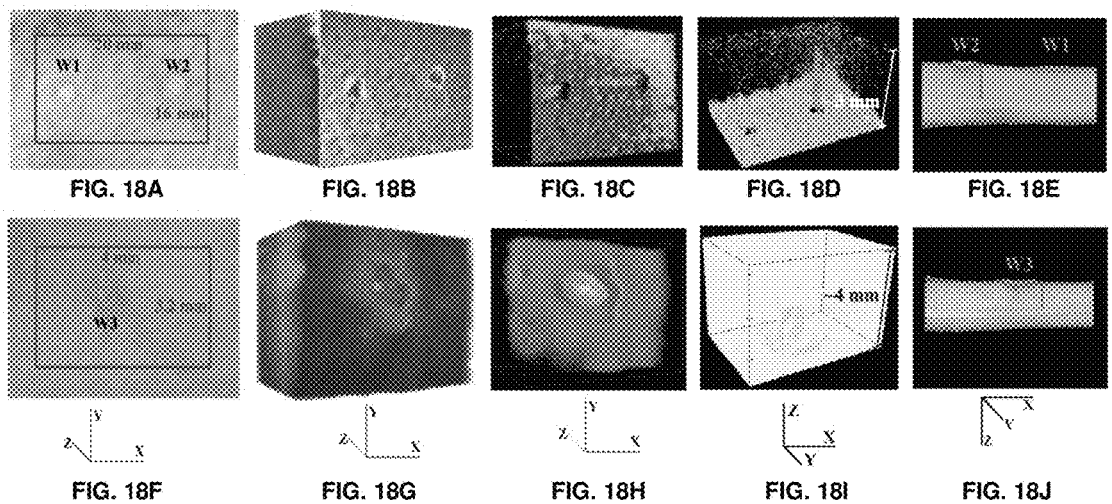
FIG. 18A  FIG. 18B  FIG. 18C  FIG. 18D  FIG. 18E
FIG. 18F  FIG. 18G  FIG. 18H  FIG. 18I  FIG. 18J
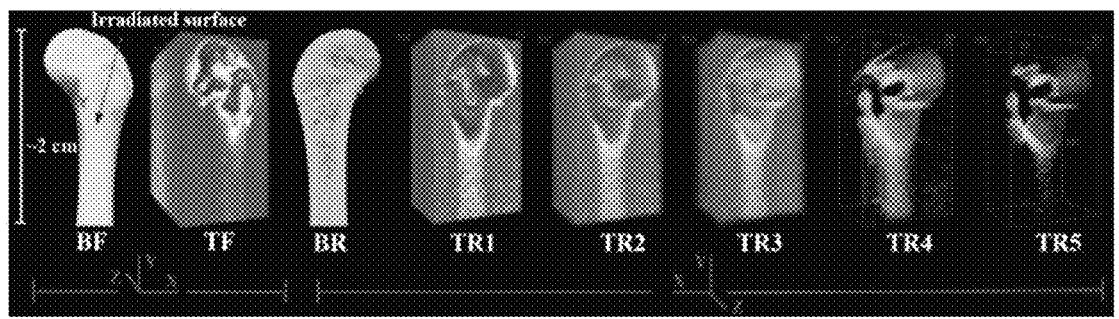
FIG. 19

US 9,810,650 B2

SYSTEMS AND METHODS FOR PERFORMING TRUNCATED-CORRELATION PHOTOTHERMAL COHERENCE TOMOGRAPHY

BACKGROUND

The present disclosure relates to thermal imaging. More particularly, the present disclosure relates to the nondestructive characterization of objects and materials.

The science of diffusion waves has been a focus of intense interest since the middle of the 19$^{th}$ century [1-3]. However, it is the latest four decades that witnessed rapid growth in this parabolic-wave-governed energy or matter transport research which encompasses several sub-disciplines such as thermal waves, diffuse photon density waves, and excited-carrier plasma waves [4-7]. In contrast to electromagnetic or acoustic waves which are described in terms of hyperbolic differential equations, diffusion waves lack wave fronts and are reflection- and refraction-less in nature [8]. Thermodynamically, diffusion occurs to minimize the free energy of a system and should be driven by a free energy gradient. Detection of distance-integrated, rather than localized, distributions of energy is a unique characteristic of diffusion-wave fields. An important feature of the physics of parabolic diffusion wave fields, both stationary and drifting, is that an energy preserving completeness relation linking the time-domain propagation of a diffusive energy impulse with a complete stationary frequency spectrum cannot be defined due to the strongly lossy character of energy migration across the contributing frequency modes. As a consequence of the loss of frequency modes, non-localization and spreading of diffusive impulses occurs at the expense of coherence between time and depth of energy propagation, leading to poor axial resolution which deteriorates with time and distance from the source and is a serious limiting factor of diffusion waves. Historically, the first attempt for localizing energy in a thermal-wave field was made by using pseudo-random binary sequence (PRBS) optical excitation followed by cross-correlation signal processing [9]. Later, the frequency modulated (FM) time delay technique was proven to have faster response and improved dynamic range compared to the PRBS scheme [10]. Significant progress in this area was made with the attainment of binary-phase-coded thermal coherence tomography (TCT) [11]. The energy localization achieved in TCT, although incomplete, enables the deconvolution of thermal responses from axially discrete sources and improves the depth resolution in thermal-diffusion wave imaging. All these methods make use of matched filtering using pulse compression, which is a traditional radar technique for enhancing range resolution and signal to-noise ratio (SNR) [12] in a hyperbolic wave field. Here, the coded signal can be described by the frequency response $H(\omega)$ of the coding filter. The frequency response of the matched filter which receives the signal is the complex conjugate $H^*(\omega)$ of the coding filter response. The output of the matched filter is the inverse Fourier transform of the product of the signal spectrum and the matched filter response:

$$y(t) = \frac{1}{2\pi} \int_{-\infty}^{\infty} |H(\omega)|^2 e^{i\omega t} d\omega \qquad (1)$$

Compared to harmonic signals, the definite advantage of a short pulse capable of maintaining flat power spectrum over a very broad bandwidth, even under diffusive attenuation losses, recently inspired the present inventors to introduce the chirped-pulse thermal-diffusion-wave radar [13]. The advantages of highly compressed output with negligible side-lobe power distribution led to much improved SNR and depth profiling capability that make this concept particularly attractive for the optothermal analysis of biological samples in which infrared absorption by water molecules and the maximum permissible exposure (MPE) ceiling [14] on the excitation fluence appreciably limit the measurable thermal-diffusion-wave signal. However, in the case of diffusion waves, the limited frequency bandwidth afforded by this coding and its inability to encompass widely varying frequency contents as time evolves and spatial coordinates change, lead to incomplete or limited localization and loss of coherence on timescales and associated spatial locations outside the completeness bandwidth. Poor efficiency or SNR and the lack of control over axial resolution, which in turn hinders the three-dimensional visualization of subsurface features, are shortcomings of these radar approaches and they are major impediments in thermal-diffusion-wave applications to systems with intricate or complex subsurface structures such as biological specimens.

SUMMARY

In various embodiments of the present disclosure, a photothermal (or thermophotonic, in the case of non-opaque materials) three-dimensional imaging modality is disclosed, which is referred to herein as truncated-correlation photothermal coherence tomography (TC-PCT). This imaging modality can exhibit a high degree of energy localization in a parabolic diffusion wave field via time-evolving filtering that is controlled by pulse delay and truncation. According to the example methods disclosed herein, photothermal radiation is detected with an infrared camera while exciting a sample with the chirped delivery of incident laser pulses (where the pulses have a fixed width), and time-dependent photothermal signal data is obtained from the infrared camera and processed using a time-evolving filtering method employing cross-correlation truncation. The cross-correlation truncation method results in pulse-compression-linewidth-limited depth-resolved images with axial and lateral resolution well beyond the well-known thermal-diffusion-length-limited, depth-integrated nature of conventional thermographic and thermophotonic modalities. As a consequence, an axially resolved layer-by-layer photothermal image sequence can be obtained, capable of reconstructing three-dimensional visualizations (tomograms) of photothermal features in wide classes of materials.

Accordingly, in one aspect, there is provided a method of performing photothermal imaging, the method comprising:
  generating an excitation chirped waveform comprising a chirped sequence of pulses;
  controlling a laser according to the excitation chirped waveform, such that the laser emits a chirped sequence of laser pulses;
  directing the chirped sequence of laser pulses onto a sample;
  detecting, with an infrared camera, photothermal radiation emitted from the sample, thereby obtaining time-dependent photothermal signal data for each image pixel of the infrared camera;
  generating a truncated chirped waveform comprising a chirped sequence of truncated pulses, wherein each truncated pulse has a pulsewidth less than that of the pulses of the excitation chirped waveform, and wherein each truncated pulse is delayed by a pre-selected time delay relative to a corresponding pulse of the chirped sequence of pulses;
  cross-correlating the time-dependent photothermal signal data with the truncated chirped waveform, thereby obtaining, for each pixel of the infrared camera, time-dependent cross-correlation data; and
  generating image data based on the time-dependent cross-correlation data.

In another aspect, there is provided a system for performing photothermal imaging, the system comprising:
  a laser;
  an infrared camera; and
  computer hardware including processor electronics configured to perform operations comprising:
    generating an excitation chirped waveform comprising a chirped sequence of pulses;
    controlling the laser according to the excitation chirped waveform, such that the laser emits a chirped sequence of laser pulses onto a sample;
    detecting, with the infrared camera, photothermal radiation responsively emitted from the sample, thereby obtaining time-dependent photothermal signal data for each image pixel of the infrared camera;
    generating a truncated chirped waveform comprising a chirped sequence of truncated pulses, wherein each truncated pulse has a pulsewidth less than that of the pulses of the excitation chirped waveform, and wherein
  each truncated pulse is delayed by a pre-selected time delay relative to a corresponding pulse of the chirped sequence of pulses;
    cross-correlating the time-dependent photothermal signal data with the truncated chirped waveform, thereby obtaining, for each pixel of the infrared camera, time-dependent cross-correlation data; and
    generating image data based on the time-dependent cross-correlation data.

In another aspect, there is provided a method of performing acousto-thermal imaging, the method comprising:
  generating an excitation chirped waveform comprising a chirped sequence of pulses;
  controlling a high-frequency ultrasound source according to the excitation chirped waveform, such that the high-frequency ultrasound source emits a chirped sequence of ultrasound pulses;
  directing the chirped sequence of ultrasound pulses onto a sample;
  detecting, with an infrared camera, photothermal radiation emitted from the sample, thereby obtaining time-dependent photothermal signal data for each image pixel of the infrared camera;
  generating a truncated chirped waveform comprising a chirped sequence of truncated pulses, wherein each truncated pulse has a pulsewidth less than that of the pulses of the excitation chirped waveform, and wherein
  each truncated pulse is delayed by a pre-selected time delay relative to a corresponding pulse of the chirped sequence of pulses;
    cross-correlating the time-dependent photothermal signal data with the truncated chirped waveform, thereby obtaining, for each pixel of the infrared camera, time-dependent cross-correlation data; and
    generating image data based on the time-dependent cross-correlation data.

In another aspect, there is provided a system for performing acousto-thermal imaging, the system comprising:
  a high-frequency ultrasound source;
  an infrared camera; and
  computer hardware including processor electronics configured to perform operations comprising:
    generating an excitation chirped waveform comprising a chirped sequence of pulses;
    controlling the high-frequency ultrasound source according to the excitation chirped waveform, such that the high-frequency ultrasound source emits a chirped sequence of ultrasound pulses onto a sample;
    detecting, with the infrared camera, photothermal radiation responsively emitted from the sample, thereby obtaining time-dependent photothermal signal data for each image pixel of the infrared camera;
    generating a truncated chirped waveform comprising a chirped sequence of truncated pulses, wherein each truncated pulse has a pulsewidth less than that of the pulses of the excitation chirped waveform, and wherein
  each truncated pulse is delayed by a pre-selected time delay relative to a corresponding pulse of the chirped sequence of pulses;
    cross-correlating the time-dependent photothermal signal data with the truncated chirped waveform, thereby obtaining, for each pixel of the infrared camera, time-dependent cross-correlation data; and
    generating image data based on the time-dependent cross-correlation data.

In another aspect, there is provided a method of performing photo-acoustic imaging, the method comprising:
  generating an excitation chirped waveform comprising a chirped sequence of pulses;
  controlling a laser according to the excitation chirped waveform, such that the laser emits a chirped sequence of laser pulses;
  directing the chirped sequence of laser pulses onto a sample;
  detecting, with an ultrasound array, ultrasound waves emitted from the sample and beamforming the received ultrasound signals to obtain spatially-resolved time-dependent ultrasound signal data from the sample;
  generating a truncated chirped waveform comprising a chirped sequence of truncated pulses, wherein each truncated pulse has a pulsewidth less than that of the pulses of the excitation chirped waveform, and wherein
  each truncated pulse is delayed by a pre-selected time delay relative to a corresponding pulse of the chirped sequence of pulses;
    cross-correlating the spatially resolved time-dependent ultrasound signal data with the truncated chirped waveform, thereby obtaining time-dependent cross-correlation data; and
    generating image data based on the time-dependent cross-correlation data.

In another aspect, there is provided a system for performing photo-acoustic imaging, the system comprising:
  a laser;
  an ultrasound array; and
  computer hardware including processor electronics configured to perform operations comprising:
    generating an excitation chirped waveform comprising a chirped sequence of pulses;
    controlling the laser according to the excitation chirped waveform, such that the laser emits a chirped sequence of laser pulses onto a sample;
    detecting, with an ultrasound array, ultrasound waves responsively emitted from the sample and beamforming the received ultrasound signals to obtain spatially-resolved time-dependent ultrasound signal data from the sample;

generating a truncated chirped waveform comprising a chirped sequence of truncated pulses, wherein each truncated pulse has a pulsewidth less than that of the pulses of the excitation chirped waveform, and wherein each truncated pulse is delayed by a pre-selected time delay relative to a corresponding pulse of the chirped sequence of pulses;

cross-correlating the spatially resolved time-dependent ultrasound signal data with the truncated chirped waveform, thereby obtaining time-dependent cross-correlation data; and generating image data based on the time-dependent cross-correlation data.

A further understanding of the functional and advantageous aspects of the disclosure can be realized by reference to the following detailed description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Embodiments will now be described, by way of example only, with reference to the drawings, in which:

FIGS. 5A-F show a set of TC-PCT images of steel block, showing (A) irradiated surface of a steel block with its co-ordinate system, (B) amplitude tomogram as observed from the blackened surface, (C) cross-sectional view obtained by slicing image (B) in the (X-Z) plane at P3, (D) rear view of the block with co-ordinates rotated by 180°, (E) amplitude tomogram as observed from the rear surface, (F) cross-sectional view obtained by slicing (E) in the (X-Z) plane at P4.

FIGS. 6A-E provide images sectioned cortical and trabecular regions, showing, (A) cross-sectional photograph of a goat rib-bone with soft tissue overlayer (labels C and T refer to the cortical and trabecular regions, respectively), (B) the irradiated tissue surface, (C) the photothermal volume tomogram observed from the tissue surface, (D) the tomogram observed from the trabecular bottom surface, (E) cross-sectional TC-PCT corresponding to (A). Some trabecular interconnections are missing because their photothermal signal strength is below the threshold defined for volume reconstruction. The graphite-adhered trabecular network has a pronounced contribution to the tomogram.

FIGS. 7A-H demonstrate bone demineralization assessment with binarized-amplitude-volume tomograms. FIGS. 7A-D show results before demineralization, showing (A) cortical layer, (B) trabecular network, (C) cortical and trabecular parts together viewed from below (here, labels C and T refer to the cortical and trabecular regions, respectively), and (D) photograph of rib cross-section before demineralization. FIGS. 7E-G show results after demineralization, showing (E) cortical layer, (F) trabecular network, (G) cortical and trabecular parts together viewed from below, and (H) photograph of rib cross-section after demineralization.

FIGS. 13A-D show the variation of mean planar amplitude (MPA) with depth below the irradiated sample surface before and after demineralization for 10-, 20-, 30- and 40-hours.

FIGS. 15A-F shows binarized amplitude TC-PCT images (A-C) and absolute amplitude tomograms (D-F) for the intact sample RB10, showing: (A,D): cortical alone; (B, E): trabecular alone; (C, F): cortical-trabecular combined (imaged area is 4×3.2 mm$^2$ and depth is ~2.8 mm). For tomograms A and D, z=0 coincides with the left face (cortical surface). For b, C, E and F, z=0 lies on the right (invisible) surface, which is the cortical-trabecular interface for B and E, and the cortical surface for E and F.

FIGS. 18A-J show the application of TC-PCT to burn-depth analysis. In all images, the Z axis (depth) is not shown on the actual scale, but has been expanded for clarity. The images show: (A) photograph of a pig's ear specimen with two burns (the red envelope is the imaged area); (B) amplitude tomogram as observed from the tissue surface; (C) amplitude tomogram with 60% transparency (the 3D spatial distribution of burn-injuries within the tissue can be observed); (D) amplitude tomogram with transparency and threshold optimized for burn depth profile inspection (the needle-like structures at the bottom (X-Y) are due to follicles without hair whose presence can be seen in (A)); (E) photograph of the burn cross-section (the red scale is ~5 mm); (F) photograph of the second sample with burn W3; (G) amplitude tomogram as observed from the tissue surface; (H) amplitude tomogram with 60% transparency; (I) amplitude tomogram with transparency and threshold optimized for burn inspection; (J) photograph of the burn cross-section (the red scale is ~4 mm).

FIG. 19 shows the variable-threshold TC-PCT amplitude tomograms for a mouse femur. Selective mapping of regions of a specific BMD range is possible by adjusting the threshold. Amplitude tomogram (TF) is developed by irradiating the cortical surface in BF. TF is rotated to view from the rear side (TR1-5). BR is the rear view photograph.

DETAILED DESCRIPTION

Figure 1A:
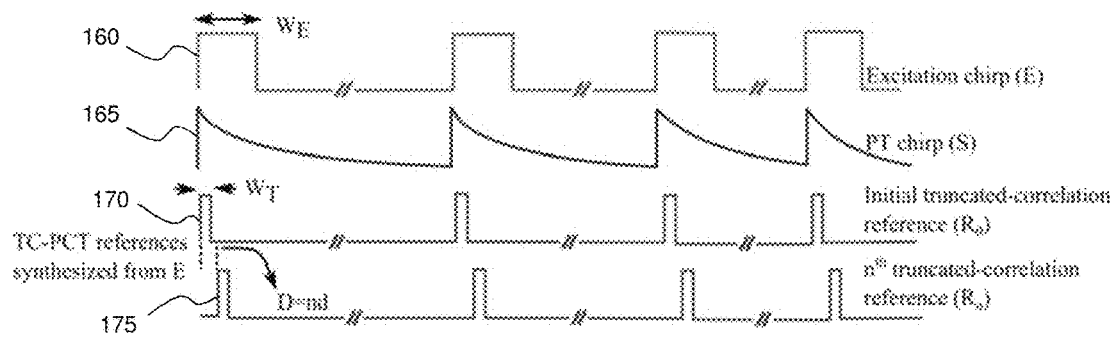
FIG. 1A is an illustration showing the timing of the waveforms employed in an example implementation of truncated-correlation photothermal coherence tomography (TC-PCT). The truncated reference chirp, synthesized from the laser excitation chirp, is subjected to controlled phase increment. The truncated pulse width is much smaller than the repetition period.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Various example embodiments of the present disclosure employ systems and methods for performing truncated cross-correlation to extract depth-dependent image data from photothermal signals. According to one example method disclosed herein, time-dependent photothermal signal data is obtained by detecting photothermal radiation emitted by a sample while the sample is excited with fixed-width laser pulses having a chirped repetition rate. The detected time-dependent photothermal signal data is processed using a time-evolving filtering method that employs cross-correlation truncation to extract depth-dependent image data from the time-dependent photothermal signal data. This method is henceforth referred to as truncated-correlation photothermal coherence tomography (TC-PCT), and various example implementations of the TC-PCT method are illustrated in the following description and examples.

Figure 1B:
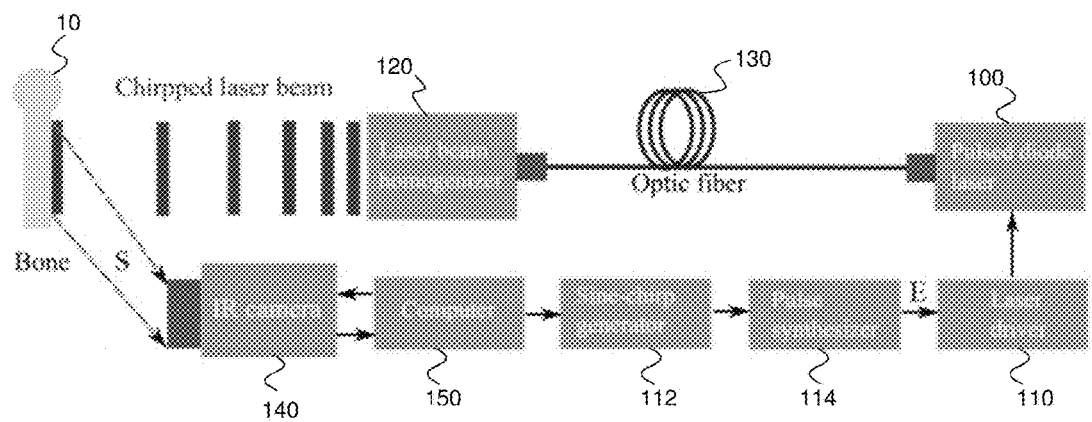
FIG. 1B is a block diagram of an example system for performing truncated-correlation photothermal coherence tomography.

An example system for performing TC-PCT is shown in FIG. 1B. The example system includes laser 100 (for example, a pulsed diode laser, which is driven by laser driver 110) that emits laser pulses, which are directed onto sample 10 for inducing a photothermal response therein. As shown in the figure, the laser pulses emitted by laser 100 may be homogenized prior to be directed onto the sample 10, for example, using beam homogenizer 120. The laser pulses emitted by the laser may be guided through a length of optical fiber 130 prior to being directed onto the sample 10.

The laser pulses are absorbed by sample 10, thereby generating a photothermal signal that is radiated by sample 10 and detected via infrared camera 140. Time-dependent photothermal signal data from camera 140 is recorded and processed, by control and processing unit (e.g. a computer) 150, in order to extract TC-PCT image data corresponding to various depths within sample 10. In one example implementation, the camera is a mid-infrared camera, such as the Cedip 520M, which has a 3.6-5.1 μm spectral response. Imaging camera 140 may be configured with active lock-in capability to detect "waveform engineered" image time sequences which are further processed to become TC-PCT tomograms.

Infrared camera 140 may be triggered by control and processing unit 150 to initiate image frame acquisition following photothermal excitation of the sample.

Figure 1C:
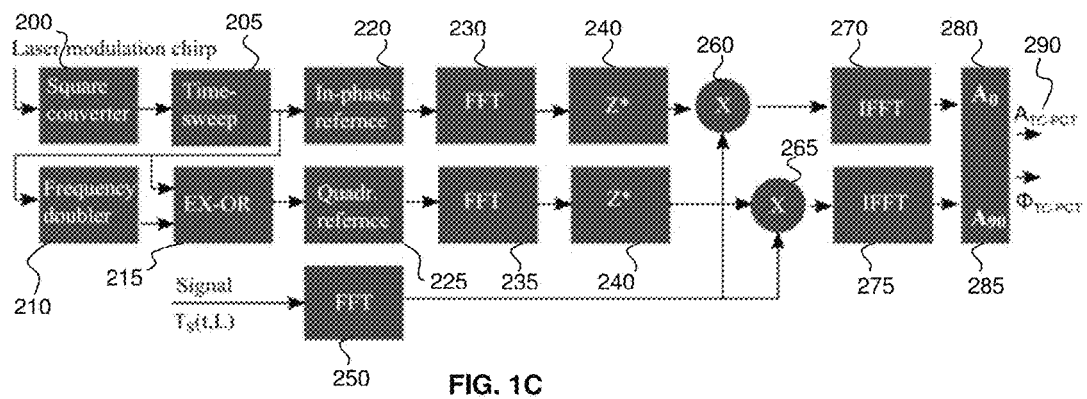
FIG. 1C is a flow diagram illustrating an example implementation of truncated-correlation photothermal coherence tomography.

In order to implement the example TC-PCT method shown in FIGS. 1A-C, the pulses emitted by the laser are chirped according to an excitation chirped waveform that is provided to laser driver 110. FIGS. 1A and 1B illustrate an example and non-limiting method of pulse chirping, in which the pulse profile 160 emitted by laser 100 is generated as a series of pulses with a constant pulse profile $W_E$, but with a chirp in the delay between pulses (i.e. a chirp in the pulse repetition rate).

In the example implementation shown in FIG. 1B, the excitation chirped waveform that is provided as input to laser driver 110 is generated in two steps. A sine-chirp generator 112 is employed to generate a sinusoidal chirp, which is then fed, as a trigger signal, to a pulse synthesizer 114, for the generation of a waveform of fixed-width pulses according to the sinusoidal chirp profile. As shown in FIG. 1A, a linear frequency modulated (LFM) train of short optical pulses (E) of pulsewidth $W_E$ is used to excite the sample. It will be understood that this example excitation chirped waveform, and the example method of generating this excitation chirped waveform, are intended to be provided as non-limiting examples, and that other excitation chirped waveforms and excitation chirped waveform generation methods may be alternatively employed.

A practical example of an implementation of the system shown in FIG. 1B includes a sine chirp synthesizer 112 (Agilent 33220A) for generating the linear frequency modulation (LFM), whose output is converted to a corresponding square chirp using a TTL Schmitt trigger circuit. A delay/pulse generator 114 (Stanford Research DG535) converts this square chirp to a pulse chirp, the pulse width being adjustable (although in the present example, the pulse width $W_E$ is fixed). This pulse chirp controls the diode laser 100 (808 nm, 40 W) and can be recorded via a high speed data acquisition module (NI PCI-5122) (interfaced with control and processing unit 150) for synthesizing the truncated reference chirp for post-processing, as described further below. The camera frames are stored with its data acquisition provision.

This chirp is effectively encoded into the time-dependent photothermal signal data that is obtained via infrared camera 140, and can be employed, via truncated cross-correlation methods, to extract depth-dependent image data. It will be understood that although the example embodiments described herein employ a linear chirp, alternative implementations may be realized using a non-linear chirp.

It will be understood that a linear frequency modulated (LFM) pulsed chirp can be synthesized from a corresponding cosine chirp such that a pulse occurs at the zero crossing of every full cycle. In other words, a conventional cosine chirp can be employed to generate a pulsed chirp. The zero-crossing time determines the position of pulses along the time scale. This form of a chirped pulse sequence is beneficial because the thermal decay following the optical pulse should decay within each period element of the chirp. It will be understood, however, that the example chirped sequence of pulses that is disclosed herein is not intended to be limiting, and that other chirp formats may be alternatively employed.

The TC-PCT process involves the post-processing of the detected time-dependent photothermal signal data in order to extract depth-dependent image data. The post processing is achieved by cross-correlation of the time-dependent photothermal signal data with a truncated chirped waveform that is synthesized according to the chirp signal that is used to control laser 100.

As described above, the TC-PCT methods described herein involve the use of truncated-correlation radar, in which the thermal relaxation chirp is cross-correlated with a split/sliced reference chirped pulse whose width is shorter than the excitation pulsewidth. FIG. 1A schematically illustrates the relationship between the laser pulses 160, the decaying time-dependent photothermal signal 165 that is detected by the infrared imaging camera, and the truncated reference chirped pulses that are employed during cross-correlation. The figure shows truncated reference chirped waveforms 170 and 175, each with a pulsewidth of $W_T$ (where $W_T < W_E$). Multiple truncated reference chirped waveforms are synthesized, with a variable delay/initial-phase (in the present example embodiment, the delay generated according to D=nd, where n=0, 1, 2, ..., and d is the delay step). These truncated reference chirped waveforms are referred to as $R_n$, where $R_0$ is the initial waveform 170 with zero delay, and $R_n$ is the nth delayed waveform.

Each of the truncated reference chirped waveforms at a fixed delay time is cross-correlated with the time-dependent photothermal signal captured by infrared camera 100, thereby employing radar pulse compression to produce two-dimensional, axially resolved, layer-by-layer images of the sample.

For example, cross-correlation of the initial truncated reference chirped waveform $R_0$, which is in phase with the laser chirped pulse waveform (160, E), with the time-dependent photothermal signal (S, 165, shown for a given pixel), will generate a surface image of the sample. In the case of $R_1$, the resulting image will be that of a near-surface (subsurface) thin layer. As the delay increases, the depth of the layer below the surface also increases.

Furthermore, it will be understood that the depth resolution or "thinness" of a truncated-correlation image layer will increase as the truncated pulse width shortens. Parameters controlling the maximum penetration depth include the starting LFM frequency, and the period/length of the chirp. For a given chirp and truncated pulsewidth, the depth range is controlled by the chirp repetition period.

As noted above, each truncated reference chirped waveform can be cross-correlated with the time-dependent photothermal signal data captured by the infrared camera, in a pixel-by-pixel manner, in order to produce two-dimensional, axially resolved, layer-by-layer images of the sample. For example, cross-correlation of the reference, which is in phase with excitation chirp, with the PT image chirp, will give a surface picture of the sample. As delay/initial-phase increases, the depth of the layer below the surface also increases. Furthermore, the depth resolution (thinness of an image layer) will increase as $W_T$ shortens. The TC-PCT is thus analogous to a bandpass filter whose operating frequency and quality (Q) factor are variable.

The time-dependent photothermal signal data (PT relaxation signal, following a pulsed excitation, is continuous in the frequency domain and during TC-PCT execution the frequency contributing the planar image keeps on decreasing with the increase in delay/initial-phase. Parameters controlling the maximum penetration depth are the starting LFM frequency and period/length of the chirp.

In some embodiments, a single truncated reference chirped waveform may be generated in order to obtain photothermal image data at a single depth within the sample. In other embodiments, two or more truncated reference chirped waveforms may be generated. As described below, the generation of multiple images at different depths may be employed to generate volumetric image data. For example, by incrementing the initial phase/delay of the split-reference chirp and sampling the radar output at a fixed position, one can obtain a sequence of time-coded data that yields a depth coded photothermal profile of the medium.

The image data can also be employed to generate time-dependent, depth-resolved images based on the photothermal data. For example, using an infrared camera, the evolution of surface temperature can be recorded and the output can be translated to a sequence of frames of two-dimensional depth-coded images with a high degree of localization. These images can be stacked to produce a volume visualization of photothermal properties of the sample. This truncated-reference-swept-correlation process in the time domain is analogous to a continuously tunable band pass filter in the frequency domain.

While the operating/central frequency of the system is controlled by the delay of the trimmed chirped-pulse with respect to the excitation pulse, the pass-bandwidth or quality factor is determined by the truncated-pulse width. In truncated cross-correlation thermal-diffusion-wave fields, the delay controls the depth while the truncated-pulse width determines the degree of energy localization (axial resolution).

It is noted that in contrast to time-domain thermal relaxation signals that lack phase, the images that are generated according to the present TC-PCT methods can provide amplitude, time-delay and phase for the matched filter, all of which can carry depth resolved energy localization information with more or less sensitivity and dynamic range. As noted above, the axial resolution is determined based on the truncated pulse duration—i.e. the shorter the truncated pulse duration, the greater the axial resolution will be due to the improvement in energy localization. Irrespective of pulse width, the delay-sweep increment determines the depth sampling interval.

It will be understood that depth-resolved image data can be obtained provided that the truncated pulse width is less than the thermal relaxation time of the material being measured. This implies that if the truncated pulse chirp were replaced by an expanded pulse chirp, such that the pulse duration became comparable with the thermal relaxation time, then a depth integrated, rather than depth resolved, thermal-wave picture of the sample will emerge through the radar channels. In such a case, the features of regular lock-in thermography [15,20] would be obtained.

FIG. 1C illustrates an example method for performing post-processing according to the TC-PCT method. As described in the examples below, TC-PCT has been implemented in a LabView environment, with a frequency domain cross-correlation algorithm for faster execution. As shown in the figure, the recorded excitation chirp is first converted to a square wave chirp at 200, and then passed through the delay-sweep module at 205, thereby generating an in-phase reference. The delay-incremented square wave chirp ($C_{1f,0}$) is then frequency-doubled ($C_{2f,0}$) at 210. Subsequently, $C_{1f,0}$ and $C_{2f,0}$ are subjected to the binary exclusive-or (EX-OR) operation at 215 to generate a quadrature square chirp $C_{1f,90}$. Truncated references $R_0$ and $R_{90}$ are synthesized from $C_{1f,0}$ and $C_{1f,90}$, respectively, as shown at 220 and 225, respectively.

A Fourier transform is then obtained for each of the truncated references, as shown at 230 and 235, respectively, and the complex conjugate of each transformed reference is calculated, as shown at 240 and 245. The complex conjugate of Fourier transformed truncated-references, both in-phase and quadrature, is then multiplied with the Fourier transform of the time-dependent photothermal signal (obtained at 250), as shown at 260 and 265. The products are inverse-Fourier transformed, as shown at 270 and 275, to generate the in-phase and quadrature TC-PCT output, shown at 280 and 285, respectively, from which the amplitude and phase can be evaluated, as shown at 290.

It is noted that there are two output cross-correlated signal channels at 290, namely $A_0$ and $A_{90}$. These can be construed to be the equivalent of in-phase and quadrature data in polar coordinates, and they can be recast as amplitude and phase. An amplitude image may be formed by determining, for each pixel, and for a given delay (i.e. at a given depth), the locus of the peak amplitude in the time-dependent amplitude (e.g. the peak amplitude in FIG. 1F). The resulting two-dimensional set of amplitude values, associated with a given delay (i.e. depth), represents a depth-resolved image. Similarly, a phase image may be generated by determining, for each pixel, and for a given delay (i.e. at a given depth), the phase value that corresponds to the amplitude peak. Furthermore, as noted above, the delay time associated with the amplitude peak may be employed to generate a depth-resolved images. It will also be understood that many other different types of images may be obtained by processing the output of the cross-correlation.

The resulting two-dimensional images are time slices with a 1-to-1 correspondence to depth slices, as determined by the truncated reference waveform pulsewidth. This is to be contrasted with conventional cross-correlation thermography, in which the cross-correlation is taken over all times, such that a number of subsurface locations can contribute to the peak—ad such methods only yield partial localization. In the example embodiments provided herein, the thinness of the truncated reference waveform pulse determines a thin subsurface spatial region for the two-dimensional image at that depth/delay, without incorporating contributions from other depths—thereby generating a truly depth-resolved image.

The truncated-correlation photothermal coherence tomography (TC-PCT) method described above is believed, by the inventors, to provide the highest energy localization modality in a parabolic diffusion wave field to-date. As noted above, TC-PCT uses a truncated-correlation pulse-chirped radar approach in which broadband thermal relaxation is cross-correlated with a truncated pulse width and delay-swept reference. The truncated pulse width determines the depth (axial) resolution while the delay with respect to the excitation chirp controls the depth range. As shown below, both parameters may be operator selectable. It has been found that among the available outputs (amplitude, initial phase, peak delay time, and zero-phase delay), the amplitude channel offers the highest dynamic range and sensitivity, capable of depth-profiling and thermal-wave reconstruction over ca. four diffusion lengths. This feature has been verified both theoretically and experimentally, as shown in the examples provided herein. Furthermore, by stacking depth-scaled planar images generated through phase incrementing the truncated coherent reference, TC-PCT can create three-dimensional visualizations of the distribution of optothermal parameters of the target similar to optical coherence tomography (OCT) but with considerably higher depth range (millimeters instead of submillimeter). The image sequence can also be binarized to generate a volume visualization whose transparency is adjustable to allow viewing the interior.

This is akin to optical coherence tomography (OCT) but with much longer coherence length and dynamic range in light-source scattering (turbid) media. It enables three-dimensional "sharp" or "crisp" visualization of subsurface features/discontinuities in systems with intricate sub-structures which is not possible with OCT or known optical or conventional photothermal imaging techniques for large classes of materials such as opaque and light scattering solids. As a further consequence of its depth resolved nature, TC-PCT also exhibits subsurface depth imaging capabilities well beyond those of conventional thermal-wave modalities (approx. by a factor of 4).

The time-evolving filtering described above leads to narrow (e.g. ultra-narrow) pulse compression linewidth, so that the falling edge of the compressed pulse carries a highly depth-resolved signature of the photothermal features of the sample, the depth being coded in terms of delay time. For example, FIG. 1F shows theoretical and experimental results of the highly compressed and side-lobe minimized truncated correlation amplitude for a 4-mm thick cortical bone slab extracted from a goat femur [22]. The measured $\mu_a$ was approx. 0.33 $mm^{-1}$ at 808 nm and was obtained using the Beer-Lambert law and a variable thickness bone wedge. Truncated pulsed chirp radar parameters, henceforth designated as chirp-1 waveform, were: starting frequency=0.2 Hz, ending frequency=0.6 Hz, chirp period=12 s, excitation pulse width=10 ms, truncated pulse width=2 ms and laser peak power=40 W. Energy per chirp was ca. 1.92 J and exposure energy density was about 0.5 $J/cm^2$, well below the maximum permissible exposure (MPE) ceiling for bone at 808 nm. The depth localized profile was time-scaled along the falling edge of the compressed pulse. As noted above, according to the TC-PCT method, a peak is generated in the cross-correlation for each truncated reference waveform delay time, effectively forcing the signal to correlate coherently with the energy existing within the gate time window. The sharp cross-correlation peak, as seen in FIG. 1F, represents the particular delay time. Another delay time will generate a similarly narrow peak at a time consistent with that delay time. As shown in FIG. 1C, the IFFT in-phase and quadrature channels, which are both time dependent, can be recast into amplitude and phase channels, each of which is associated with a sharp peak.

Figure 1D:
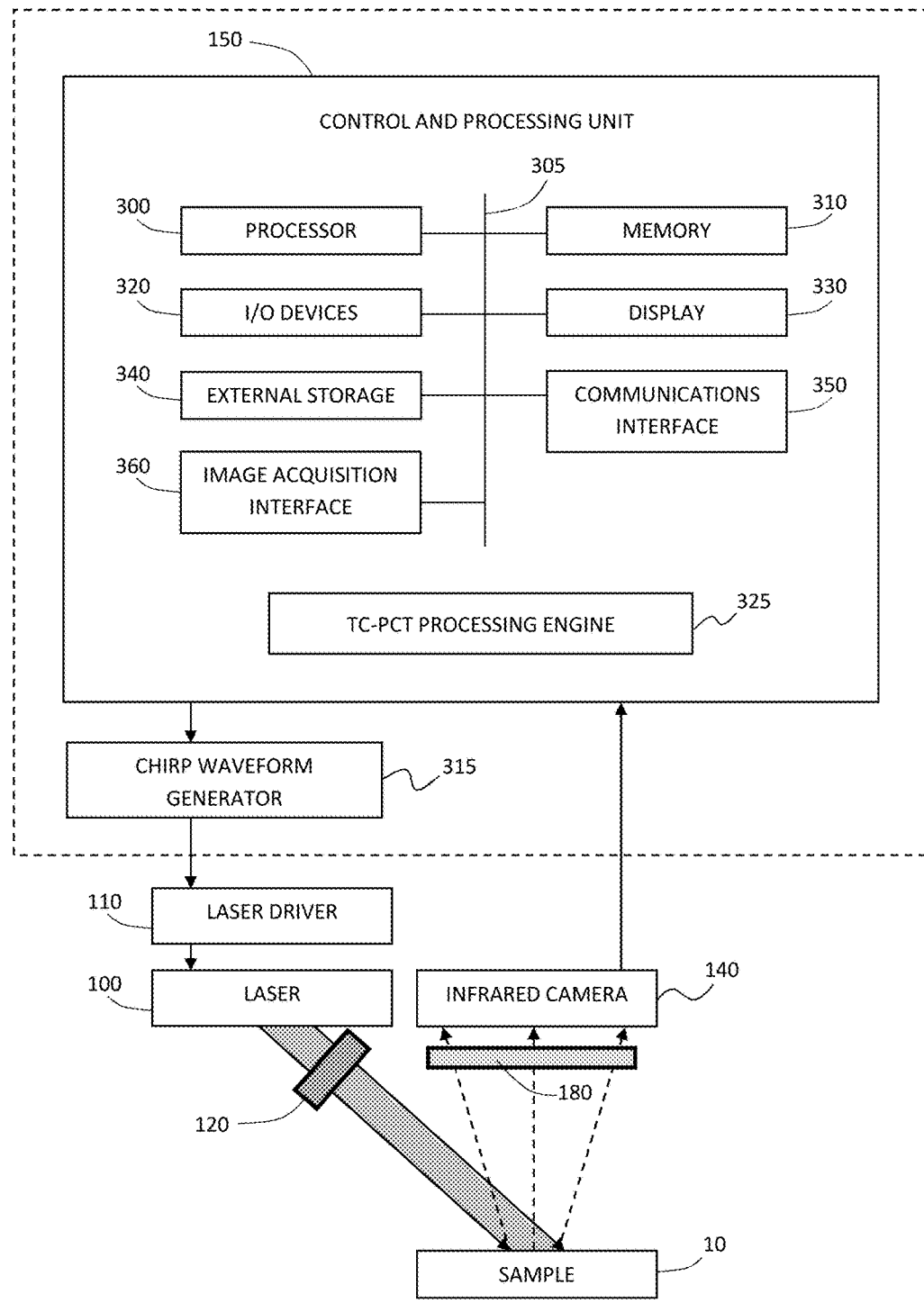
FIG. 1D is a block diagram of another example system for performing truncated-correlation photothermal coherence tomography.

Referring now to FIG. 1D, another example system is provided for performing TC-PCT imaging. As in FIG. 1C, the system includes a laser 100 (driven by laser driver 110) that directs pulses onto sample 10, where the pulses are delivered in a chirped format, based on a chirped waveform provided by chirp waveform generator 315. Chirped waveform generator 315 may, for example, be configured to generate constant-width pulses with a chirped pulse delay, as illustrated in FIGS. 1A and 1B. Laser 100 may have an integrated laser driver, or a separate laser driver 110, as shown in FIG. 1B. The emitted laser beam may optionally be homogenized by beam homogenizer 120, and additional beam conditioning optics, such as, but not limited to, lenses, filters, mirrors, apertures, beam collimators and/or beam diffusers, may be employed. The emitted photothermal radiation is detected by infrared imaging camera 140, and a filter 180 may be provided to filter extraneous optical radiation incident on infrared imaging camera 140.

Imaging camera 140 is an infrared imaging camera configured to detect photothermal radiation emitted from the sample. As discussed above, a suitable imaging camera is a mid-infrared imaging camera, such as the Cedip 520M.

As shown in FIG. 1D, in one embodiment, control and processing unit 150, may include a processor 300, a memory 310, a system bus 305, an image acquisition interface 360 (such as a frame grabber), one or more input/output devices 320, and a plurality of optional additional devices such as communications interface 350, display 330, and external storage 340.

It is to be understood that the example system shown in the figure is not intended to be limited to the components that may be employed in a given implementation. For example, the system may include one or more additional processors.

One or more components of control and processing unit 150 may be provided as an external component that is interfaced to a processing device. For example, image acquisition interface 360 may be an external interface, or may reside on a card directly interfaced with a computing device. Furthermore, as shown in the figure, chirp waveform generator 315 may be included as a component of control and processing unit 150 (as shown within the dashed line), or may be provided as one or more external devices, as shown in FIG. 1C.

Embodiments of the disclosure can be implemented via processor 300 and/or memory 310. For example, the functionalities described below can be partially implemented via hardware logic in processor 300 and partially using the instructions stored in memory 310. Some embodiments are implemented using processor 300 without additional instructions stored in memory 310. Some embodiments are implemented using the instructions stored in memory 305 for execution by one or more general purpose microprocessors. Thus, the disclosure is not limited to a specific configuration of hardware and/or software.

As shown in the figure, control and processing unit 150 includes TC-PCT processing engine 325, which comprises algorithms for performing the TC-PCT methods described herein, stored as computer-readable instructions in memory 310 to be executed by processor 300.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Figure 1E:
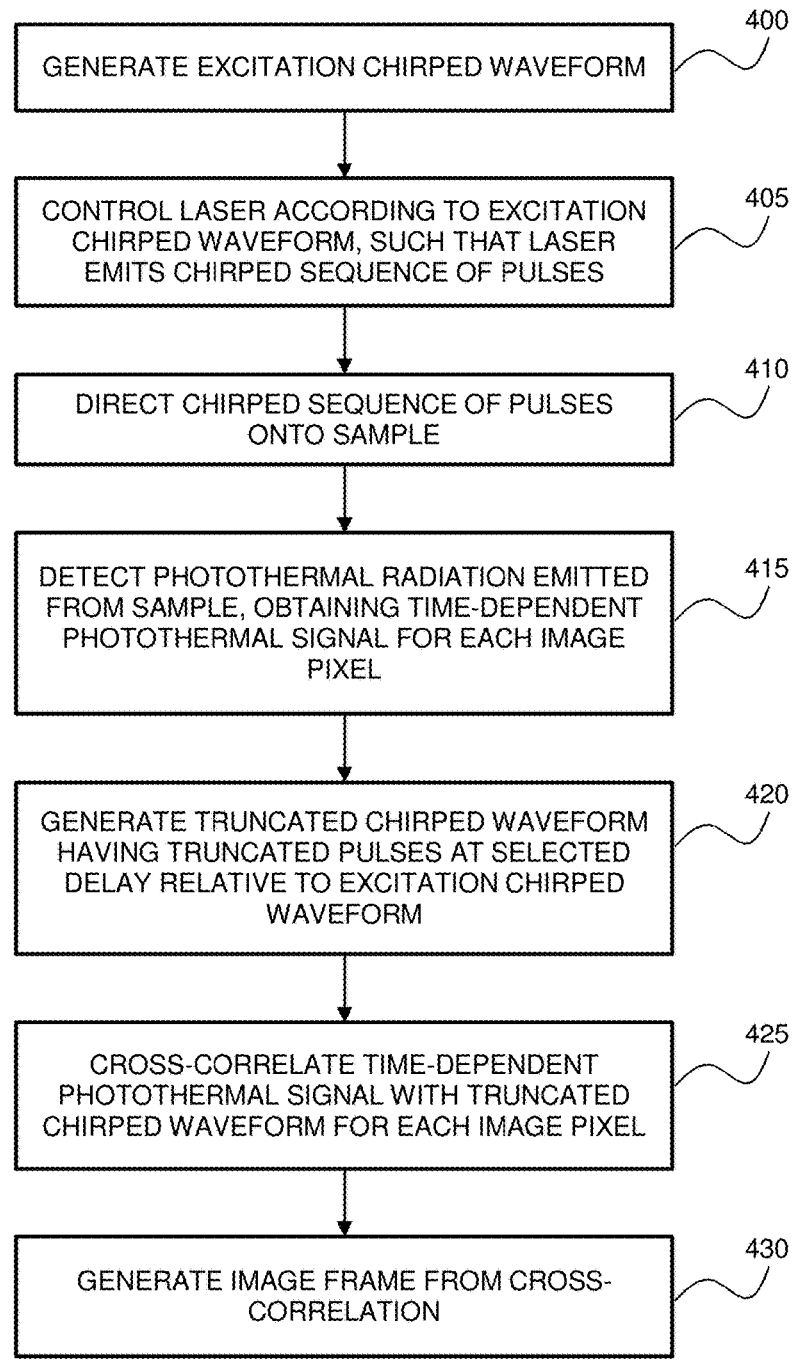
FIG. 1E is a flow chart illustrating an example method for performing truncated-correlation photothermal coherence tomography.
Figure 1F:
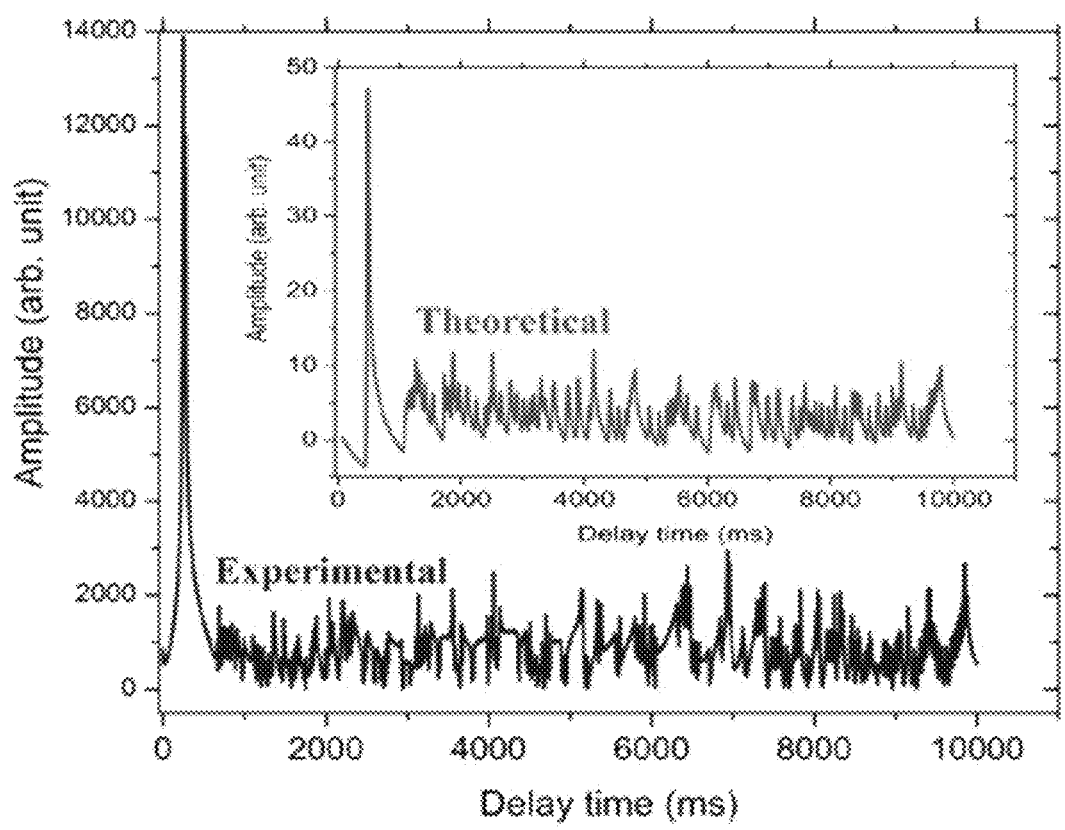
FIG. 1F plots the theoretical and experimentally measured results for the TC-PCT output.

Referring now to FIG. 1E, a flow chart is provided that describes an example embodiment for performing TC-PCT. In step 400, an excitation chirped waveform is generated. The excitation chirped waveform may take the form of a set of fixed width pulses having a chirped repetition rate, as described in the preceding examples. It will be understood that other chirped pulse profiles may alternatively be employed. The resulting chirped sequence of pulses is then delivered onto the sample at step 410, and the resultant photothermal radiation is detected by the infrared imaging camera at step 415. The camera detects multiple image frames, such that a time dependent signal is obtained for each pixel of the camera.

The time-dependent photothermal signal obtained from each pixel is then processed according to the TC-PCT method, as shown in steps 420 and 425. At least one truncated chirped waveform is generated at step 420, when each truncated chirped waveform is generated to produce a truncated version of the excitation chirped waveform, such that each pulse of the excitation chirped waveform is generated within the truncated chirped waveform as a narrower pulse at a given delay. Each truncated pulse has a pulsewidth less than that of the pulses of the excitation chirped waveform, and each truncated pulse is delayed by a pre-selected time delay relative to a corresponding pulse of the chirped sequence of pulses.

Each truncated chirped waveform is then cross-correlated with the time-dependent photothermal signal for each pixel in step 425. This may be performed, for example, using the methods described above involving in-phase and quadrature multiplication in the frequency domain. The resulting cross-correlated data, obtained for each pixel and for each truncated chirped waveform (i.e. for each delay), is then employed to generate one or more depth-resolved images, as shown in step 430.

As described above, the depth-resolved images may be prepared according to a wide variety of parameters, including amplitude, phase, and delay. The depth resolved images may be further processed according to a wide variety of image processing algorithms in order to obtain different renderings of the image data. For example, when multiple depth-resolved images are combined to obtain volumetric image data, the volumetric image data may be processed according to a binarized thresholding algorithm in order to render the volumetric image data in a binarized format for display.

Planar-Image Sequence Formation and Three-Dimensional Reconstruction

A sequence of 2D truncated-correlation amplitude images at increasing depths below the surface can be generated by incrementing the value of delay/initial-phase.

As noted above, the repetition time of the chirp defines the maximum depth probed, form which thermal information arrives at the surface. This is due to the thermal conduction time $t \sim Cx^2/\alpha$, where x is the depth probed, and a is the thermal diffusivity of the material, and C is a factor close to unity. In the above equation, x would be the only depth involved in conventional lock-in thermography. In the example TC-PCT methods disclosed herein, however, depth is controlled by the narrow time gate opened at a fixed delay, as prescribed by the delay values of the various truncated reference waveforms that are employed for cross-correlation. This use of truncated reference waveforms at different delays (and therefore different depths) gives rise to sequences of image sheets which comprise the 3D volume of the image when stacked up.

Figure 3:
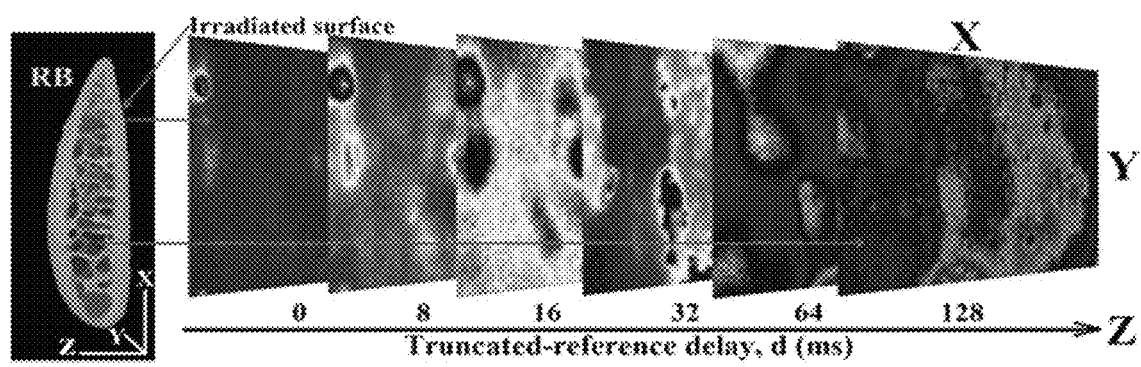
FIG. 3 shows a series of depth scaled planar images for a rib bone (RB) at various time delays. Below every image shown is the respective delay in ms. $W_T$ was 2 ms. The last plane is ~1.6 mm below the irradiated surface.

As example, typical 2D images obtained for a rib ($\sim 5\times 1.6\times 0.45$ cm$^3$; average cortical thickness $\sim 0.7$ mm) with chirp-1 (the starting and ending frequencies for LFM were 0.2 and 0.6 Hz, respectively with a period of 12 s) excitation are shown in FIG. 3. Imaged dimensions are 4 and 3.2 mm along the X and Y directions, respectively. $W_T$ was 2 ms. The zero-delay (0 ms) corresponds to the surface layer and a delay of 128 ms defines a plane that is $\sim 1.6$ mm below the surface (as estimated based on the above equation relating delay to depth). These sequences can be stacked to generate a three-dimensional visualization and the stack can be binarized to reconstruct a binary amplitude-volume tomogram (BVT). Binary amplitude-volume tomograms are independent of the absolute PT amplitude and they depict the presence or absence (binary 1 or 0) of thermal wave power within the sample. ImageJ software was used for all image processing tasks [23]. For binarization, unless otherwise specified, Huang algorithm [23-25] can be used, which offered the optimum noise immunity and sensitivity to demineralization.

Depth coded two-dimensional amplitude images were stacked to form the three-dimensional TC-PCT amplitude tomograms. For binary amplitude tomography, every planar image was first binarized such that amplitudes lower than a threshold value were treated as binary '0' and those above it as '1'. These binary planar images were stacked and then subjected to volume reconstruction such that only two physical states (absence or presence of a photothermally active source) appear in the resulting tomogram. The threshold value and image transparency are adjustable.

Theoretical Model of TC-PCT Detection

One of the major outcomes of the propagating wave description of diffusion-wave fields is the existence of a complex wavenumber and the dispersive characteristics stemming from the fact that phase velocity is frequency dependent: In terms of the transport parameter (diffusivity a for thermal waves) and angular frequency (w), the phase velocity is defined as allowing faster diffusive wave propagation at higher frequencies, which is also true for hyperbolic waves. The frequency spectrum of a photothermal relaxation signal following a short pulsed excitation is continuous. The surface transient amplitude is, therefore, scaled in terms of depth below the surface such that the early transient strength corresponds to shallow regions while late portions correspond to deeper zones.

Although the full thermal-wave frequency spectrum in a given configuration is set by the excitation optical pulse, the truncated cross-correlation process provides a time-evolving filter which preserves coherence in the part of the frequency spectrum within the instantaneous time window. Therefore, the effect of correlation truncation is to preserve the energy within the instantaneous frequency bandwidth with no or minimal loss despite the diffusive nature of the signal. Over the entire thermal relaxation process, the cumulative effects of energy preservation within the wide spectral bandwidth spanned sequentially through the time-evolving filter make the parabolic diffusive response spectrum resemble the spectral characteristics of a propagating lossless hyperbolic wave field and its response to cross-correlation and pulse compression image processing familiar from radar science.

Based on the hyperbolic wave description of diffusion waves, a theoretical formalism can be established to elucidate the features of these distinct/independent channels of amplitude, time-delay and phase in TC-PCT. A homogeneous sample of thickness L is considered, in which thermal diffusion waves propagate without "reflection" (accumulation or depletion) except at the irradiated surface-air boundary.

Any energy accumulation/depletion at the rear surface is ignored in this work, as back surfaces are typically deep enough so as not to significantly affect the characteristics of TC-PCT. Assuming bulk optical absorption, for one-dimensional heat diffusion the spectral element of the surface temperature of the sample following optical excitation can be expressed in the frequency domain as:

$$\hat{T}_s(\omega, t, L) = \frac{[1-R]I\mu_a\gamma\eta}{4k\sigma(\omega)} \int_0^L e^{i\omega t} e^{-[\mu_a + \sigma(\omega)]x} dx = \frac{[1-R]I\mu_a\gamma\eta}{4k} \left\{ \frac{1 - e^{-L[\mu_a + \sigma(\omega)]}}{\sigma(\omega)[\mu_a + \sigma(\omega)]} \right\} e^{i\omega t} \quad (2)$$

Here, R is the surface reflectivity at the excitation wavelength, I is the optical intensity, k is the thermal conductivity, $\mu_a$ is the optical absorption coefficient, $\gamma$ is the thermal wave transmission coefficient at the irradiated surface-air interface and $\eta$ is the light-to-heat conversion efficiency of the sample. $\sigma(\omega)$ is the thermal wavenumber at angular frequency $\omega$. Following pulsed excitation, the resulting transient temperature distribution at the sample surface is spectrally continuous and can be evaluated from the frequency spectrum, equation (2), using the inverse Laplace Transform:

$$T_s(t, L) = \frac{[1-R]I\mu_a\gamma\eta}{4k} \frac{1}{2\pi i} \int_{\Gamma-i\infty}^{\Gamma+i\infty} \left\{ \frac{1 - e^{-L[\mu_a + \sigma(s)]}}{\sigma(s)[\mu_a + \sigma(s)]} \right\} e^{st} ds \quad (3)$$

in which, $s = i\omega$. Contour $\Gamma$ is selected to the left of all poles in the complex plane, so that the system is stable to its right. Equation (3) can be evaluated through Laplace inversion:

$$T_s(t, L) = \frac{[1-R]I\mu_a\gamma\eta\alpha}{4k} e^{t/\tau_t} \left[ \text{erfc}\left(\sqrt{t/\tau_t}\right) - \text{erfc}\left(\frac{L}{2\sqrt{\alpha t}} + \sqrt{t/\tau_t}\right) \right] \quad (4)$$

Here, $\tau_t = 1/\alpha\mu_a^2$ is an optothermal time constant indicating heat conduction from a depth equal to the optical penetration length, and erfc refers to the complementary error function. For optical chirp generation, a pulsed semiconductor laser can be used, the current feed line of which has a finite inductance. At higher currents (a few tenths of an Ampere or more) the back emf across the feed line introduces significant rise and fall times that are not negligible compared to the pulse width. So, the optical intensity of the excitation pulse is approximately modeled as a Gaussian temporal profile:

$$I(t) = I_0 e^{-\frac{1}{2}\left(\frac{t}{\xi}\right)^2} \quad (5)$$

The pulse duration is adjusted through the Gaussian characteristic time constant $\xi$. A linear frequency modulated (LFM) pulsed chirp can be synthesized from the corresponding cosine chirp such that a pulse occurs at the zero crossing of every full cycle determined by:

$$\omega_1 t' + k t'^2 = (4n+1)\frac{\pi}{2} \quad (6)$$

Here, $\omega_1$ is the starting angular frequency, n=0, 1, 2, ... and $k = (\omega_2 - \omega_1)/T$ is the sweep rate. $\omega_2$ and T are the ending frequency and period of the LFM, respectively. The zero-crossing time $$t' = \frac{-\omega_1 + \sqrt{\omega_1^2 + 2\pi k(4n+1)}}{2k} \quad (7)$$

specifies the position of pulses along the time scale.

The in-phase reference chirped pulse ($R_0$) is set up through the convolution ($\otimes$) of the intensity Gaussian with a delayed Dirac delta impulse time series $$R_0 = \left\{ \sum_{n=0}^{p} \delta\left[t - \left(\frac{-\omega_1 + \sqrt{\omega_1^2 + 2\pi k(4n+1)}}{2k}\right)\right] \right\} \otimes I_0 e^{-\frac{1}{2}\left(\frac{t}{\xi}\right)^2} \quad (8)$$

Here, p is the number of pulses to be generated. Similarly, the quadrature reference chirp ($R_{90}$) is synthesized from a sine LFM chirp:

$$R_{90} = \left\{ \sum_{n=0}^{p} \delta\left[t - \left(\frac{-\omega_1 + \sqrt{\omega_1^2 + 8n\pi k}}{2k}\right)\right] \right\} \otimes I_0 e^{-\frac{1}{2}\left(\frac{t}{\xi}\right)^2} \quad (9)$$

By convolving the thermal transient at the sample surface, equation (4), with the delayed in-phase delta impulse series, the resulting chirped-transient surface temperature, $T_{CS}(t,L)$, can be obtained:

$$T_{CS}(t, L) = \left\{ \sum_{n=0}^{p} \delta\left[t - \left(\frac{-\omega_1 + \sqrt{\omega_1^2 + 2\pi k(4n+1)}}{2k}\right)\right] \right\} \otimes \frac{[1-R]I(t)\mu_a\gamma\eta\alpha}{4k} e^{t/\tau_t} \left[ \text{erfc}\left(\sqrt{t/\tau_t}\right) - \text{erfc}\left(\frac{L}{2\sqrt{\alpha t}} + \sqrt{t/\tau_t}\right) \right] \quad (10)$$

The in-phase/quadrature output of the chirped-pulse photothermal radar ($Rad_{0/90}$) is calculated through the excitation-response cross-correlation as $$Rad_{0/90} = R_{0/90} * T_{CS}(t, L) \quad (11)$$

The radar amplitude ($A_{Rad}$) and phase ($\phi_{Rad}$) can be estimated as $$A_{Rad} = \sqrt{Rad_0^2 + Rad_{90}^2} \text{ and } \phi_{Rad} = \tan^{-}(Rad_{90}/Rad_0). \quad (12)$$

Simulation of Amplitude, Delay Time, and Initial Phase Channels of TC-PCT on the Depth of Absorber Below Sample Surface The energy localization of the present thermal-wave modality offers superior axial resolution throughout the diffusive relaxation process and is thus capable of subsurface imaging of systems with intricate structures. One example application of the methods disclosed herein is the three-dimensional visualization of bones for the purpose of non-invasive early diagnosis of osteoporosis, especially the trabecular structure through cortical and soft tissue overlayers[18].

Figure 2A:
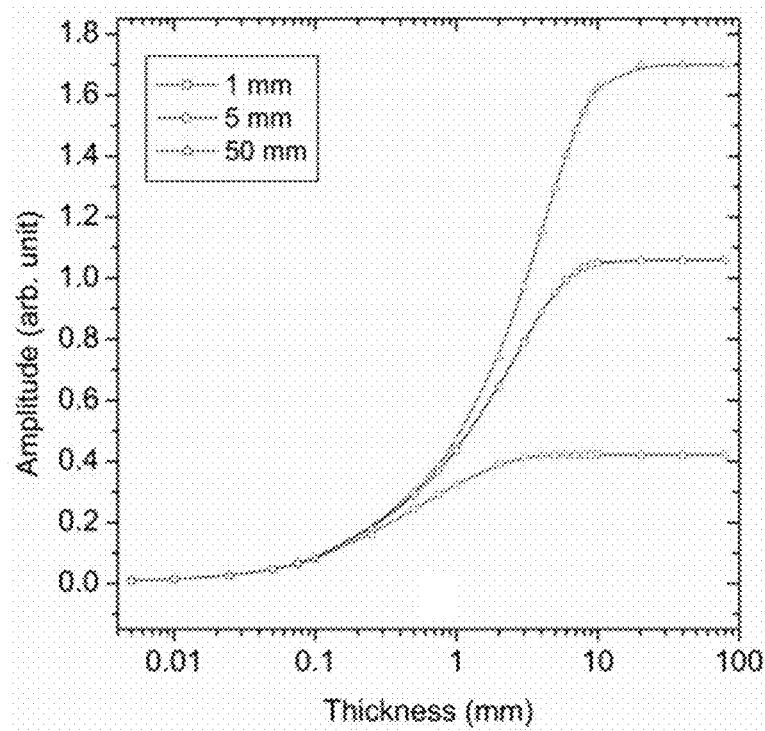
FIGS. 2A-C plot the results from a simulation of the truncated-correlation radar parameters on the absorber depth below the sample surface for optical absorption lengths ($l_a=1/\mu_a$) 1, 5 and 50 mm, showing (A) variation of amplitude, (B) variation of initial phase, and (C) variation of peak time-delay.
Figure 2B:
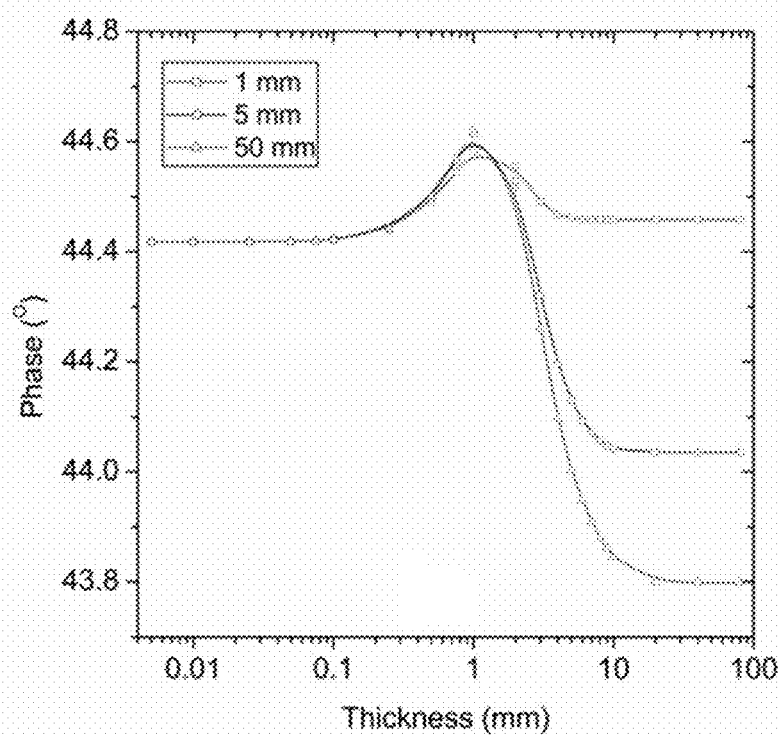
Figure 2C:
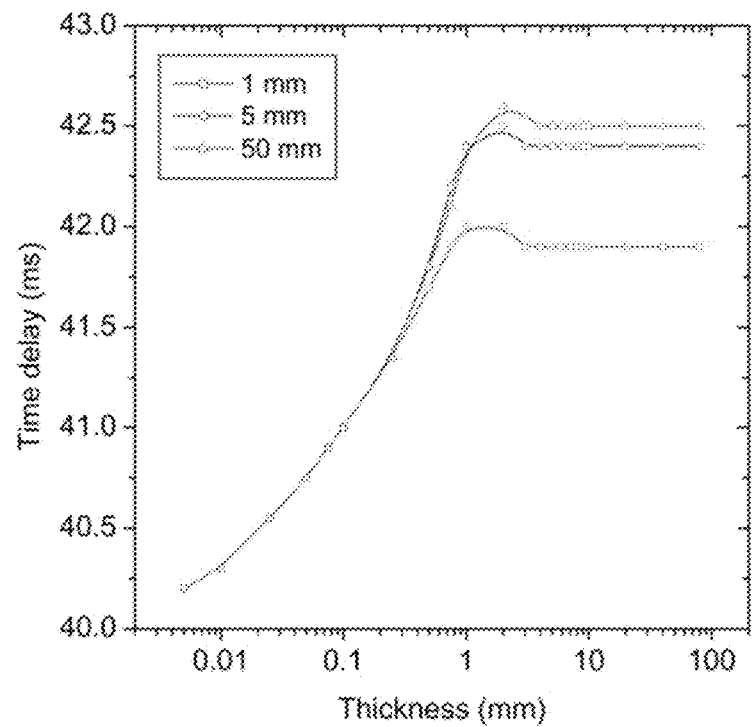

FIGS. 2A-C show the theoretical dependence of amplitude, delay time and initial phase (phase for which delay is zero) channels on the depth of signal-generating absorbers below the sample surface. For simulation, a diffusivity of $5 \times 10^{-7}$ m$^2$s$^{-1}$ and a range of absorption coefficients (at 808 nm) 0.2-1.0 mm$^{-1}$ are considered, typical of human bones. A third value of 0.02 mm$^{-1}$ was also used as an extreme case of optical transparency in tissues. Starting and ending chirp frequencies are 0.1 and 0.5 Hz, respectively. Chirp period is 25 s and half power pulse width is approx. 5 ms, the reciprocals of these durations being the lower and upper frequency limits of the chirp power spectrum. Under these conditions the thermal diffusion length ($l_d = \sqrt{2\alpha/\omega}$) in bone assumes a maximum and minimum of approximately 1.9 mm and 28 μm, respectively. As $\mu_a$ increases, the source of thermal-wave generation approaches the surface and consequently the thermal centroid moves closer to the plane of detection, because the peak delay time which is related to $\tau_t$ is anti-correlated with the optical absorption coefficient. For depths smaller than the longest diffusion length (1.9 mm), the delay time for a given absorption coefficient increases with sample thickness or with the position of the thermal-wave centroid within the sample. This is the region in which thermal-wave interference exists due to confinement within the sample. As the thickness approaches the diffusion length, interference effects produce a maximum and the delay remains saturated for depths greater than ~3.5 mm, effectively indicating a semi-infinite configuration. This means that the delay channel theoretically carries depth information up to a thickness of about two diffusion lengths. The initial phase becomes minimum around the longest diffusion length, as interference effects tend to disappear and contributions to the thermal centroid from the back-surface interactions (accumulation or depletion) become negligible. For optical absorption length $l_a = 1$ mm, when the thickness is greater than the thermal diffusion length, the sample is thermally and optically thick and the phase tends to saturate at a depth of $\sim(l_d + l_a)$. If $L > l_a > l_d$, then phase saturation occurs around 8 mm ($4l_d$) and is independent of $l_a$, in agreement with the known photothermal response of optically and thermally thick solids[19]. Phase dynamic range in excess of four diffusion lengths is, however, limited due to the lack of uniqueness in the vicinity of $L = l_d$. So, phase tomograms based on TC-PCT are distorted by interference among multiple layers, the strength of which is high near one diffusion length. The peak-amplitude channel approaches a saturation value around a depth $\sim(l_d + l_a)$ if $l_a = 1$ mm. For $l_a > l_d$, like the initial phase, the amplitude channel carries depth information up to about four diffusion lengths. The amplitude decreases with decreasing $l_a$ as the thermal gradient is higher for shorter depths. In this case, the rate of energy transfer by diffusion into the colder bulk (heat sinking) of the sample is higher than that for extended heating (higher values of $l_a$). The amplitude channel has the key advantage of high dynamic range and sensitivity based on a one-to-one correspondence with the thickness, thus paving the way for a unique depth reconstruction over about four diffusion lengths. This is the maximum depth ever attained in the evolution of thermal-diffusion-wave physics.

Axial and Lateral Resolution of TC-PCT

The photothermal signal, in general, carries information about the sample's optical and thermal properties in a composite or coupled manner [4,5]. For optically transparent materials such as most biological specimens, relative magnitudes of L, ϵ and $l_d$ ($\epsilon = 1/\mu_a$) control the photothermal response and it changes with the tissue-type. The relative magnitudes may change at different probe locations for the same sample due to biological heterogeneities. For this reason, the nature of TC-PCT image formation cannot be attributed to optical inhomogeneity alone. Instead, the coupled opto-thermal response along with sample geometry characterizes this process. In this sense, TC-PCT can be considered to be, at least in part, a functional imaging modality rather than a purely structural imaging modality. Since the thermal diffusion length is inversely correlated with the square root of frequency, higher resolution imaging would be possible at higher frequencies that demand shorter excitation pulsewidth. However, this will limit the depth range. Due to the cross-coupled opto-thermal signal generation mechanism, the easiest approach for estimating the axial and lateral resolution of TC-PCT is do it experimentally measure the resolution for a given material and chirp.

The axial resolution of TC-PCT is primarily controlled by the temporal width of truncated-reference pulse and the sample thermal diffusivity. Therefore, the resolution is material-dependent and increases as the truncated-reference pulsewidth decreases. However, the shortest possible pulsewidth may be limited by the speed of the IR camera. For example, the camera employed for the experiments described herein had a temporal resolution of ~2.7 ms. The minimum truncated-reference pulsewidth was fixed to 2 ms. For evaluating the axial resolution in bone, the chirp-1 waveform was considered. A mechanically polished, ~100 μm thick, cortical bone slab (30×10 mm$^2$) extracted from the goat femur already mentioned was used as the sample. An absorbing mark was drawn on the back surface using graphite and the sample was wetted to prevent direct radiative coupling of IR photons. TC-PCT was performed by irradiating (808 nm) the front surface with several truncated-reference pulsewidths: 2, 4, 6, 8, 10 and 12 ms. Given that bones are highly heterogeneous in their physical properties, TC-PCT was obtained at different locations. On an average, the back absorber mark appeared in the TC-PCT image for widths greater than 8 ms. For a 200-μm thick bone slab, this occurred at a ~16 ms pulsewidth. Extrapolating this response, a bone axial resolution of ~25 μm for 2-ms reference was estimated. In comparison, in steel, the resolution was found to be ~700 μm, a consequence of its higher diffusivity (see Example 2 for details). It is noted that higher axial resolution is achievable using faster cameras that permit the use of more narrowly truncated references.

Visual inspection was made to assess the lateral resolution. This was achieved by examining the binarised amplitude TC-PCT of an intact goat rib. The object dimension (area imaged on the bone surface) was 4.0×3.2 mm$^2$. With 100% magnification the corresponding image dimension (area of the tomogram) is 69.4×55.5 mm$^2$ (measured using GIMP 2.8.2). The measured image dimension of a well resolved trabecular element at a depth of ~2 mm below the surface (within the white circle) is ~1.8 mm. This corresponds to an object dimension of ~103 μm.

At some other locations, superior resolution is observable. Here, the amplitude data is binarized such that those above and below a threshold can be designated as Boolean '1' and '0', respectively, to depict the physical presence or absence of thermal-wave power at a point within the sample. The binarised 3D data is subjected to surface-mesh formation to visualize the volume distribution with adjustable transparency. This binarized amplitude tomogram is independent of the absolute PT amplitude and has advantages in the structural examination of bones. A detailed discussion on the features of binarised amplitude bone TC-PCT is described in [Kaiplavil, S., Mandelis, A., Wang, X. & Feng, T. Photothermal tomography for the functional and structural evaluation, and early mineral loss monitoring in bones. *Biomed. Opt. Express* (Accepted).]. Example methods of binarization are described in ref. 26. It is evident that trabecular structures laterally thinner than 100 μm have been resolved. For a given material, imaging area and chirp parameters, the lateral resolution is controlled by the camera resolution which, for the camera employed in the present experiments, is 320×256 pixels.

Another relevant performance figure is the speed of operation or analysis time. This is mainly controlled by the chirp period. The use of longer chirps improves the extent of energy localization [12] and the depth-range, although it slows down the imaging procedure, both data capture and reconstruction. The imaging field (area) can be arbitrarily increased provided the camera resolution is sufficiently high to maintain good TC-PCT image quality. The performance figures. of comparable imaging modalities will be discussed in the following examples, in the context of the several case-study applications.

Various example applications of the embodiments disclosed herein include non-destructive evaluation (NDE) of industrial materials and in non-invasive biomedical imaging, including solids with intricate sub-structures, specifically sub-surface holes in steel, trabecular bone structure through cortical and soft tissue overlayers, structural changes in animal bones following artificial osteoporosis (demineralization bone loss), and burn depth profiles in tissues. In particular, the following examples show that TC-PCT exhibits high sensitivity to cortical bone density which is very promising for near-surface bone (wrist, tibia, calcaneus, etc.) osteoporosis clinical imaging, as there is no need for light penetration into the deeper trabecular region. The ability of this modality to penetrate sub-surface regions below skin and fat layers bodes well for the TC-PCT imaging counterpart's future in-vivo use on human bones covered with soft tissue.

In another example application of the imaging methods disclosed herein, a non-ionizing quantitative volumetric marker, thermal wave occupation index (TWOI), is introduced for monitoring bone mineral density (BMD) variation. If the truncated-co elation pulsewidth is <<total reference phase increment, then TWOI is independent of the pulsewidth. This marker was found to be more sensitive than the μCT-measured BMD for monitoring low demineralization levels in animal rib bones. This suggests the utility of TC-PCT for early osteoporosis diagnosis.

Another notable feature of the bone TC-PCT is the intensity scaled bone tomography that enables the mapping of regions within a specific BMD range. Axial and lateral resolutions are found to be ~25 and 100 μm, respectively, which can be enhanced through instrumental improvements. The current depth range (~3.8 mm) is the highest in the field of photothermal imaging to-date and is sufficient to meet the requirements of small animal diagnosis. Deep-penetrating bone TC-PCT is expected to find applications in regular clinical diagnosis as well as in space missions for BMD monitoring of astronauts.

As described below, the TC-PCT computational slicing method has enabled the independent analysis of cortical and trabecular regions and the comparison of these results with the respective μCT images. Analogous to X-ray morphometric parameters, a 3D marker (TWOI) and a new 2D parameter, mean planar amplitude (MPA), both derived from the TC-PCT image, have been defined and estimated for goat rib bones demineralized at intervals of 10-40 hours using EDTA solution. For shorter intervals, 10 and 20 hours, both TC-PCT and μCT markers follow the same trend. For higher extent of demineralization, 30 and 40 hours, both the μCT and TC-PCT results show anomalous behavior. However, this is not a matter of prime concern since such severe demineralization is unlikely to occur naturally in living bones.

A direct comparison of tomograms derived using TC-PCT and μCT has revealed the superior dynamic range of the former. However, comparison of TC-PCT with other modalities with respect to structural imaging should be made carefully: Depending on the resolution of the IR camera, distribution of thermophysical properties of the sample and the frequency bandwidth of the TC-PCT image there will be a limit on the possible lateral resolution for a given threshold of binary TC-PCT reconstruction. This limit clearly characterizes the conditions under which purely structural imaging is possible for bone using this modality. As far as the application of TC-PCT for in-vivo bone diagnosis is concerned, an immediate possibility is the case of femur (or similar bones) of small animals like mice for which the soft tissue over-layer thickness is not large (1-2 mm). The use of a more sensitive camera, longer chirp periods and higher laser peak powers could improve the depth profiling capability, the subsurface penetration depth of thermal-wave response remains a key factor and is currently limited to 4 mm. The axial resolution, which is ~25 μm, can be enhanced using shorter truncated-reference pulsewidth and faster cameras Suitable contrast agents are expected to offer substantial sensitivity enhancement in the presence of soft-tissue and skin overlayers.

While the preceding embodiments relate to photothermal based TC-PCT image processing, it will be understood that the embodiments disclosed herein may be adapted to the embodiments involving ultrasonic generation or detection.

In one example embodiment, thermal waves may be generated using an ultrasound source instead of an optical source, and the resulting thermal radiation may be detected using an infrared camera. Such a method may be referred to as acousto-thermal coherence tomography (TC-ACT).

Figure 20A:
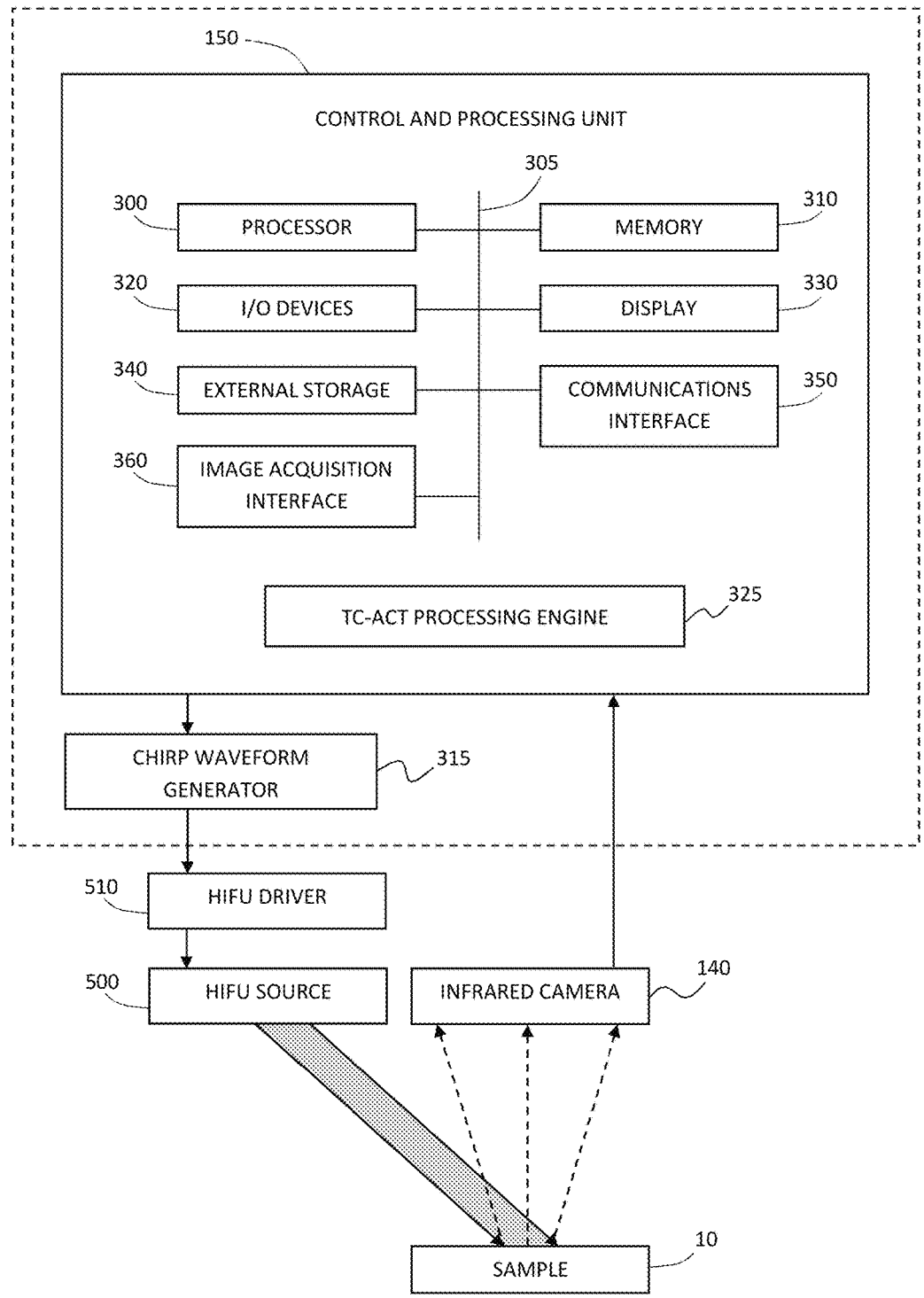
FIG. 20A is a block diagram of an example system for performing truncated-correlation acousto-thermal coherence tomography.

An example implementation of such an embodiment is illustrated in FIG. 20A, which is similar to FIG. 1D, but where the laser 100 (and associated driver 110) has been replaced by high-frequency ultrasound (HIFU) source 500 (e.g. with a bandwidth of approximately 1-5 MHz) and associated driver 510. HIFU source 500 emits a focused pulsed-ultrasound chirped train of pulses, in a manner similar to the emission of the chirped train of laser pulses emitted by laser 100 in FIG. 1D. HIFU source 100 is therefore employed as a heating source of controllable penetration depth and exposure area (for example, power-limited high intensity focused ultrasound). As in the photothermal embodiments, the resulting thermal infrared radiation is measured using infrared camera 140, and the acousto-thermal signal data received from infrared camera 140 is processed according to the embodiments described above, where one or more truncated chirped reference waveforms are cross-correlated with the acousto-thermal signal data in order to obtain depth-resolved image data. One potential benefit of this approach is that optical scattering effects are avoided. This arrangement generates a thermal transient after each pulse of the chirped ultrasound pulse train, with the remaining process being as shown in FIG. 1A (and following a method based on FIG. 1E).

While the preceding example embodiment employed ultrasound for the generation of thermal waves, it will be understood that in other example embodiments, ultrasound detection may be employed, and the resulting detected ultrasonic signal data may be processed according to the cross-correlation methods disclosed herein. In one example implementation, a pulsed laser may be employed to direct a chirped pulse train onto the sample and thereby generate photoacoustic ultrasonic waves in addition to photothermal radiation. Such an example embodiment may be referred to as truncated correlation photoacoustic coherence tomography (TC-PACT).

Figure 20B:
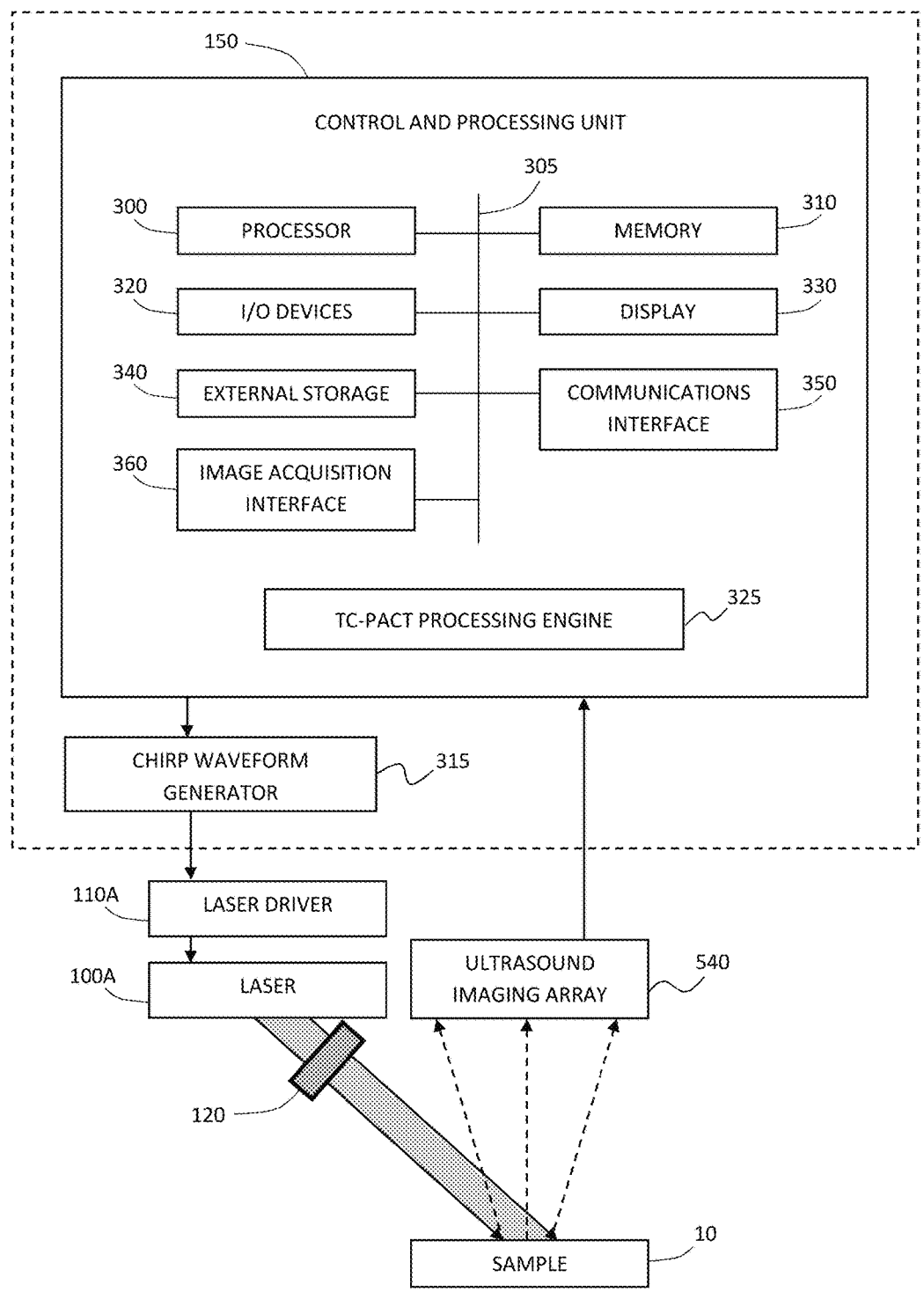

FIG. 20B illustrates an example TC-PACT system, in which the infrared detector 140 of FIG. 1D has been replaced with an ultrasonic imaging array 540. Such an ultrasonic imaging array may for formed from a plurality of ultrasonic imaging elements have a bandwidth in the range of approximately 1-10 MHz. Laser 100A (driven by laser source 110A) may have a fixed pulsewidth on the nanosecond scale, for example, between approximately 10 and 100 ns, or for example, between approximately 25 and 75 ns, or, for example between approximately 40 and 60 ns. Laser source 100A generates, through optical absorption, the emission of ultrasound waves, resulting in the emission of an ultrasonic relaxation transient following the laser pulse. Cross-correlation of the detected ultrasound waves with one or more truncated chirped reference waveforms is performed, in a manner similar to that described in FIGS. 1A and 1E. While the waveforms occur on a much more rapid timescale than the waveforms of photothermal implementations, their processing can nonetheless be implemented using control and processing unit 150 that is equipped with suitable frame detection hardware, such as using hardware available from National Instruments.

The following examples are presented to enable those skilled in the art to understand and to practice embodiments of the present disclosure. They should not be considered as a limitation on the scope of the disclosure, but merely as being illustrative and representative thereof.

EXAMPLES

Example 1: Proof of Concept: TC-PCT Imaging of Cortical Bone Slab

Figure 4:
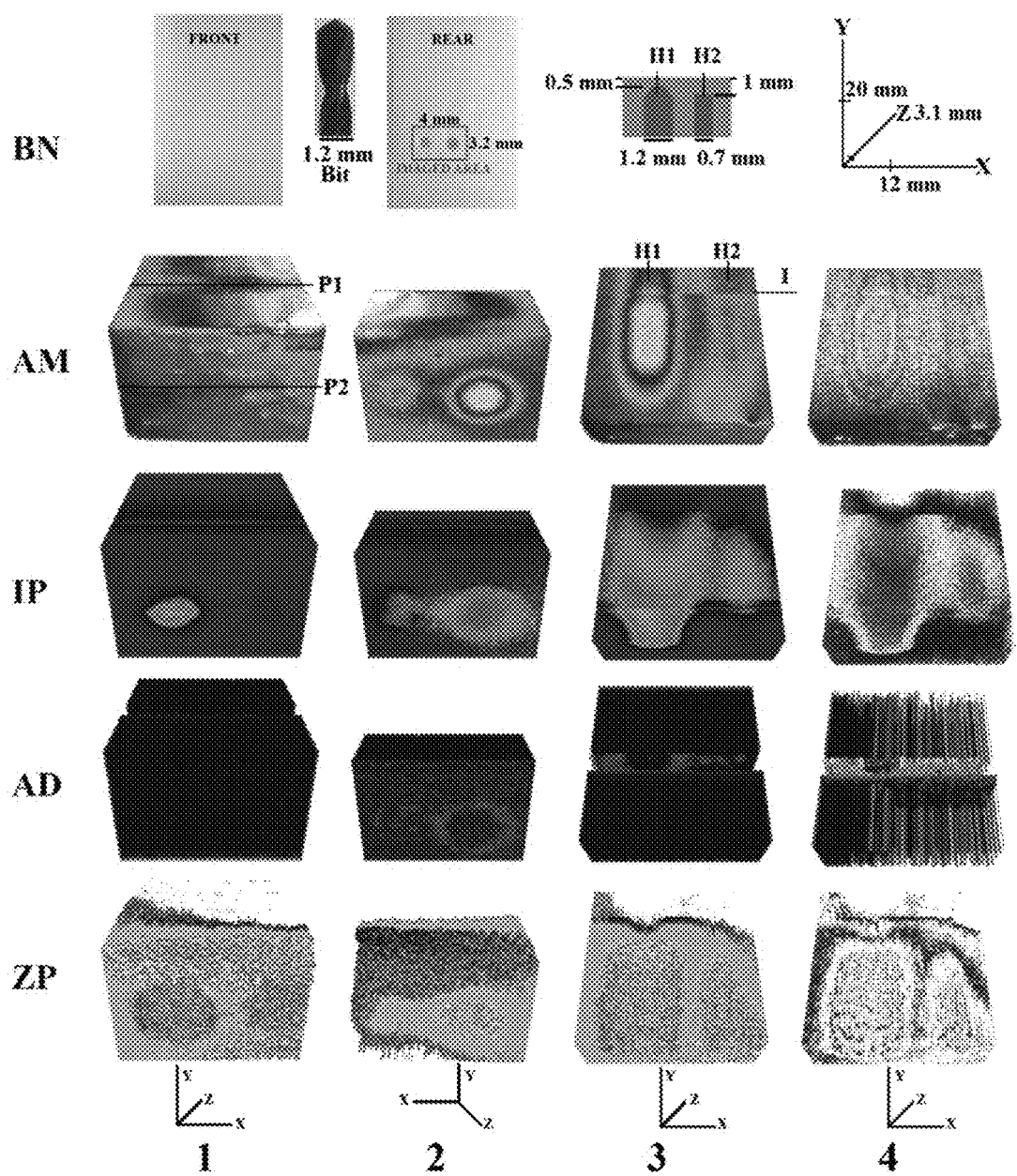
FIG. 4 provides a set of truncated correlation tomograms of a polished cortical bone. BN 1-4: Goat bone sample, geometry of holes and coordinate system for BN 1. AM 1-4: amplitude, IP 1-4: initial phase, AD 1-4: amplitude delay and ZP 1-4: zero-crossing phase delay tomograms.

Truncated correlation tomograms were recorded (FIG. 4) for a polished cortical bone slab extracted from the aforementioned goat femur. Sample dimensions were 12, 20 and 3.1 mm along the X, Y and Z axes, respectively (as shown in BN 1-4 in FIG. 4). Two holes with 1.2 (H1) and 0.7 (H2) mm diameters were drilled from the rear side such that the bone layer thickness above the holes was ~0.5 and 1 mm for H1 and H2, respectively. Two red nylon wire sleeves were inserted tightly into these holes to ensure localized optical absorption. The imaged area was 4×3.2 mm$^2$ on the front (X,Y) surface. The camera was operated at 370 frames/sec. Chirp-1 waveform with a sweep-delay step of 2 ms was used to generate a stack of 150 two-dimensional pseudo-color images, allowing a 300-ms sweep duration. A three-dimensional relief was composed from these stacks using ImageJ software [23]. All tomograms (image stack volumes) in column-1 were vertically sliced at P1 across the top (X-Y) plane and the half volume was rotated by 180° to generate the tomographic images in column-2, depicting the corresponding interior cross-sections. The image volume in column-1 was further sliced horizontally at P2 on the (X-Z) plane to generate column-3 which shows the depth resolving capability of this imaging modality. Column-4 is the edge-detected [25] version of column-3, which enhances the boundaries and provides better sensitivity to the geometry of optothermal inhomogeneities. H1 was made with a sharp tipped regular drill bit and H2 with a flat-tip grinding bit. The bit-tip feature is clearly revealed in the depth-resolved reconstruction in AM 3, top feature of H1. H2 is somewhat obscured by a strongly absorbing inhomogeneity near the top-right corner, which is a characteristic feature of most biological specimens. In any case, the capability of this modality to resolve subsurface features hidden below this photothermally active overlayer is further demonstrated in the figure. The energy accumulation at the rear bone-air boundary is observable in the (X-Z) plane around layer l. The resolution of the initial-phase tomogram (IP 1-4) is severely deteriorated by the non-unique response around a depth equal to the diffusion length, as well as by limited dynamic range, particularly for shallow regions which in turn lead to depth-overlapping near the front surface. However, this signal channel would be useful to probe deeper regions, preferably below one diffusion length, as the phase variation with depth is within an experimentally resolvable band. The time-delay 3D-tomogram (AD 1-4) carries depth information for a thin segment. The high temporal uncertainty (~2.7 ms) of the IR camera limits the axial resolution of this channel. In any case, the depth range is limited to about one diffusion length. Here, zero-phase delay (yet another channel) refers to a dynamic steady-state for the corresponding layer across which there is no net thermal-wave propagation. Because the rest of the material except for the layer of interest is not in thermal steady-state at any time, this channel leads to a quasi-static thermal volume imaging. Despite limited axial resolution, this dynamic steady-state energy distribution is sensitive to subsurface features (ZP 1-4).

Example 2: TC-PCT Imaging of Opaque Materials

The ability of truncated-correlation photothermal coherence tomography to interrogate the subsurface features of strongly absorbing samples such as metals has been verified by considering the response of a surface-blackened steel block (6×4.5×3 cm$^3$) with multiple holes (0.5 cm diameter) drilled from the bottom to align axially along the direction of one-dimensional thermal wave propagation (FIG. 5A). Holes h1-5 which are resolved in the amplitude tomograms with chirp-1 waveform excitation and 2-ms truncated reference, have steel overlayer thickness of about 0.27, 0.45, 0.62, 1.18 and 1.68 mm from the top, respectively. The tomogram (image stack volume) is sliced along P3 in the (X-Z) plane for viewing holes h1-3 (FIG. 5C). Holes h1 and h2 are clearly visible through the black layer, which is a consequence of the higher (compared to bone) thermal diffusivity of steel that makes the diffusion time of flight across the steel overlayer above h1 and h2 shorter than the temporal resolution of the camera. The tomogram is further sliced at P4 in the (X-Z) plane, FIG. 5E, to expose holes h4 and h5, FIG. 5F. In support of the abovementioned time-offlight hypothesis, h4 and h5 are axially resolved even though progressive significant signal attenuation has decreased the depth-profiling image contrast SNR. In general, higher diffusivity materials would need an appropriately higher speed IR camera for improved axial resolution in this tomographic approach. SNR, and hence depth range, can be increased by using higher laser peak power and/or a more sensitive camera. Employing longer chirps is yet another solution.

Example 3: Non-Ionizing Tomography of Bone: Volume Tomograms of Bone-Tissue Matrix To further explore the possibilities of bulk and surface imaging of absorbing samples through TC-PCT, the problem of the diagnosis of bones undergoing skeletal diseases was considered, particularly osteoporosis. In this context, it is worth emphasizing the high MPE compatibility advantage of the pulsed chirped radar [13]. The task was to construct, through cortical and tissue overlayers, a 3-D visualization of the photothermal features of a trabecular (cancellous) bone volume where demineralization occurs at an early stage of osteoporosis [27]. A goat rib bone with ~1.2 mm cortical thickness was masked with ~0.6 mm thick chicken breast tissue wrapped over it (FIGS. 6a and b) to simulate a soft tissue overlayer, and was excited with chirp-1 waveform. The imaged area was ~4×3.2 mm², FIG. 6B. A mild graphite powder coating was applied to the trabecular back to ensure absorption property resemblance with living bones containing marrow (hemoglobin absorption). Laser irradiation impinged from the top surface (imaging plane) of the chicken breast layer. Reconstructed binary volume projections [25] as observed from the soft tissue surface, the trabecular back and the vertical cross-section are shown in FIGS. 6C, 6D and 6E, respectively. Here, an envelope is reconstructed for the binary opto-thermophysical volume of the sample from the amplitude tomogram. Thickness non-uniformity as well as localized variations in the thermal-wave impedance along the tissue-bone interface can be observed in FIG. 6E. The cortical layer is well resolved and so are the trabecular interconnections below. The resolved depth in bone is about 3.6 mm.

Example 4: TC-PCT Sectioning of Cortical and Trabecular Regions and Inspection of Artificially Induced Bone Loss Another significant advantage of TC-PCT is the ability to image sectioned cortical and trabecular regions for slice-by-slice analysis. This is accomplished by suitably selecting the number of 2-dimensional image slice sequences used for volume reconstruction. Bone demineralization monitoring efficiency, a crucial parameter in osteoporosis diagnosis research, has been examined for assessing the potential of this modality in the context of non-invasive and non-ionizing medical diagnostics. A goat rib piece (~4.0×1.5×0.5 cm³) with cortical thickness 0.7 mm was chemically etched for 10 hours using 0.5 M ethylenediaminetetraacetic acid (EDTA) diluted with an equal volume of distilled water. The EDTA solution produces a very slow and gentle decalcification and its mild solution (pH 8) has been widely used in the literature for simulating artificial osteoporosis [28-30]. Since the dependence of the degree of demineralization on the etching parameters such as EDTA concentration, etching time, etc., was not precisely known, this was a non-standardized demineralization process.

FIG. 7 shows the TC-PCT binary volume images (4.0× 3.2×2.8 mm³) of the rib sample, before (FIGS. 7A-C) and after (FIGS. 7E-G) demineralization, with cortical and trabecular regions separated and together. The bone was irradiated on the top cortical surface which was the plane of imaging. Here, binarized [25] TC-PCT amplitude tomograms are used for volume reconstruction and 50% layer transparency is maintained to see the interior. FIGS. 7A-C clearly show the trabecular network resolved through the light scattering cortical layer. In FIGS. 7E-G, well resolved changes to the cortical and trabecular regions due to chemical demineralization can be observed. The finding of excellent TC-PCT sensitivity to cortical bone density changes, despite the fact that they represent only a small fraction of osteoporotic density changes in human bones which are more pronounced in the trabecular network, is very promising for in-vivo early bone osteoporosis diagnostic imaging applications of this technology, as there is no absolute need for light penetration into the trabecular region. This aspect is well adapted to the relatively shallow sub-surface penetration ability of thermal waves and points to future clinical use of this technology for non-invasive imaging of near-surface human bone density such as wrist, calcaneus and tibia.

Example 5: Thermal Wave Occupation Index (TWOI): A Marker for Non-Ionizing Early Demineralization Monitoring and its Absolute Nature A rib sample (~50×16×4.2 mm³; ~0.7 mm cortical thickness) was demineralized for known time intervals (0.5, 1, 2.5, 5, 10, 20 and 30 hours) and chirp-1 TC-PCT analysis was performed after each treatment ($W_T$=2 ms) to generate 120 planar images. Imaged area was 4×3.2 mm². The first 30 images were used for reconstructing the BVT of the cortical layer and the next 90 sequences for the trabecular region. This ratio of sequences was determined by visually examining the onset of the trabecular signature in 2D images. The combined cortical-trabecular tomogram was made using the entire 120 sequences.

Figure 8:
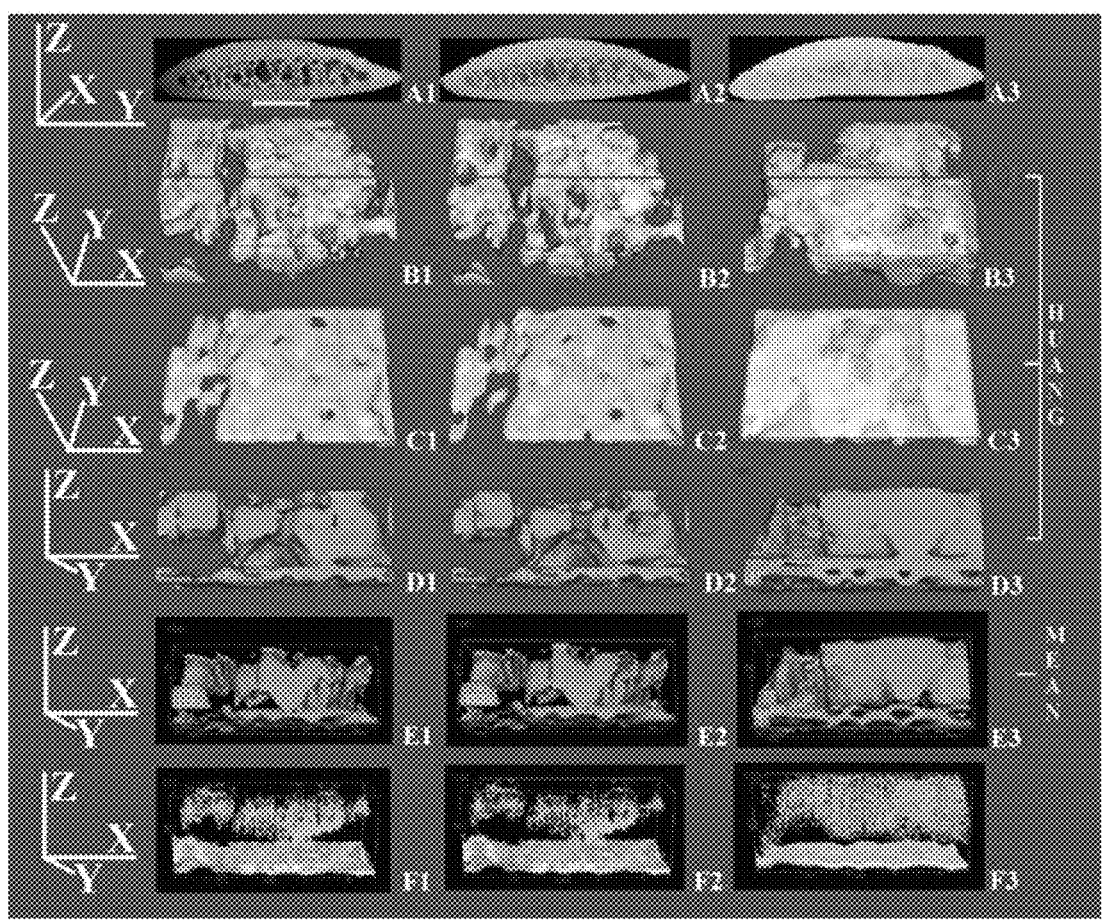
FIG. 8 provides TC-PCT images of a demineralized goat rib, showing: A1-3: cross-sectional photographs of intact, 0.5- and 20-hour demineralized sample (the yellow scale in A1 corresponds to the width of the image (3.2 mm)); B1-3: binarized amplitude tomogram of the trabecular region for samples A1-3; 01-3: binarized amplitude tomogram of the cortical layer for samples A1-3; D1-3: cross-section of the combined cortical-trabecular regions obtained by slicing B1-3 along PQ in the (X-Z) plane (see text) (laser irradiation was shone from the bottom cortical surface, which was the plane of imaging; B, C and D series were generated using Huang binarization algorithm); E1-3: counterpart of D1-3, binarized using mean-threshold algorithm; F1-3: threshold-adjusted absolute amplitude TC-PCT from which D1-3 and E1-3 were derived.

Results obtained for the intact (A1), 0.5- (A2) and 20- (A3) hour demineralized samples are shown in FIG. 8. The irradiated bottom cortical layer (C1-3) and the approx. 2-mm thick trabecular section above it (B1-3) were reconstructed independently and in tandem. The combined tomogram was sliced along PQ (marked on the trabecular section) in the (X-Z) plane and the rear half is projected in D1-3 to see the interior. Tomograms E1-3 are the counterparts of D1-3, binarized using mean-threshold algorithm instead of Huang's. Images F1-3 are obtained by adjusting the threshold, to see the cortical geometry clearly, in absolute amplitude TC-PCT from which D1-3 and E1-3 are derived.

Figure 9A:
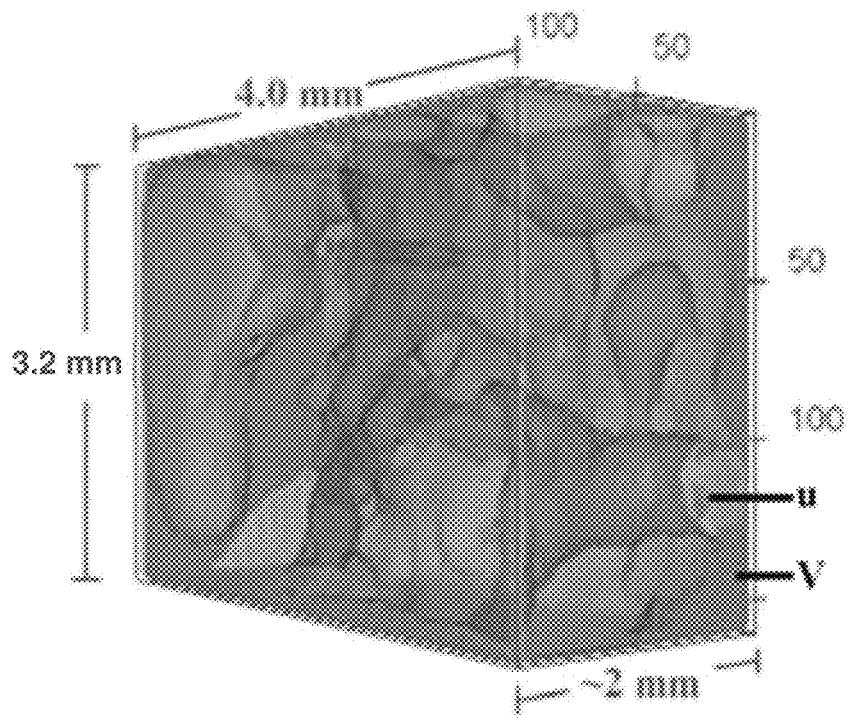
FIG. 9A shows volumes of thermal-wave occupation and its rectangular envelope for a goat rib sample.

Since the thermal wave field properties are strongly thermal diffusivity dependent which is a function of density, a measure of the volume occupied by the thermal wave power should be indicative of the mineral density distribution (or in general the degree of demineralization) within the bone. The TWOI is defined for a BVT of arbitrary volume. It is estimated for a regular volume envelope within the bone specimen (FIG. 9A). It is defined as the ratio of the volume occupied by the binarized thermal wave field (u) to the total volume of the quadrangular envelope (V) surrounding the photothermally activated region of the bone:

$$\text{TWOI} = u/V \tag{13}$$

In the illustration, the bluish box is the volume enveloping the binarized thermal wave distribution (yellow).

For a given excitation conditions, the binarized TC-PCT properties of a sample are controlled by $W_T$ and the total delay ($d_{max}$). $d_{max}$ refers to the phase difference between the first and the last truncated-references and it determines the probed depth.

Figure 9B:
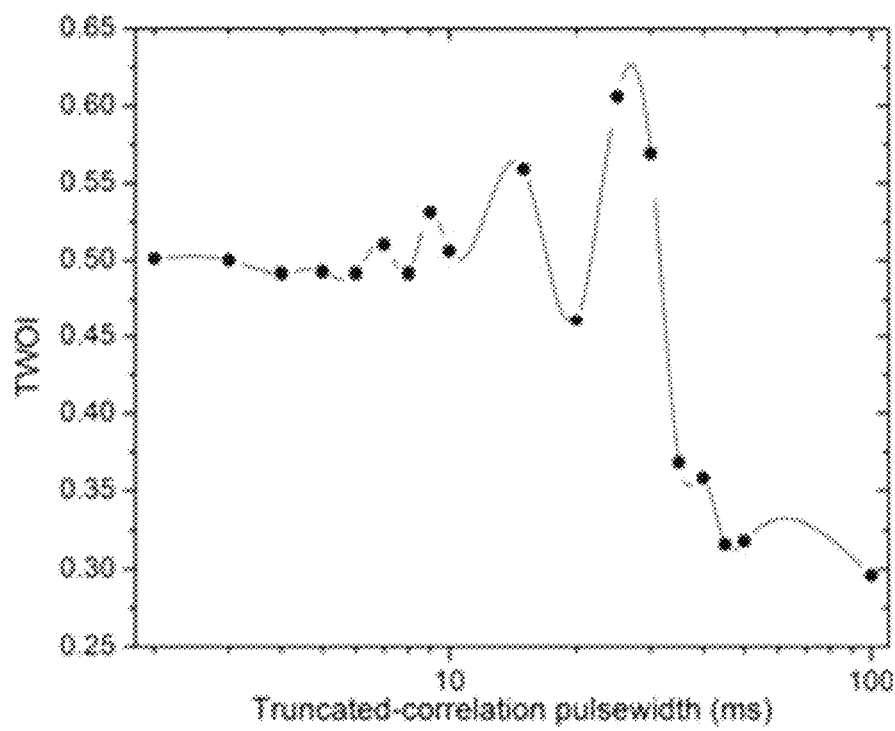
FIG. 9B shows the dependence of TWOI of a rib sample, excited with chirp-1 waveform, on the truncated-correlation pulsewidth for 200 ms total delay. The spline interpolation (blue line) is the characteristic step-response of an under-damped harmonic oscillator. The stability is better than 98.5% for a pulsewidth of 6 ms or less.
Figures 10A, 10B, 10C, 10D:
FIGS. 10A-D shows binarized amplitude TC-PCT of a rib sample reconstructed using different truncated-correlation pulsewidths (shown below the tomograms). Total delay is 200 ms that corresponds to a depth of ~2.5 mm in bone. Letters T and C in the 2-ms tomogram indicate trabecular and cortical regions. As $W_T$ increases the degree of energy localization comes down and the uncertainty in the estimation of TWOI increases. The sample was illuminated on the cortical surface. All these tomograms have the same coordinate system, shown at bottom left.

The influence of $W_T$ and $d_{max}$ on the estimation of the TWOI of a sample has been investigated by reconstructing the BVTs of a rib sample, excited using chirp-1, for $W_T$ varying in the range 2~100 ms and $d_{max}$ fixed at 200 ms. In all cases, to ensure sweep (axial) continuity, the delay increment was the same as the pulsewidth. $d_{max}$=200 ms corresponds to a depth of ~2.5 mm in bone. Estimated values of TWOI as a function of $W_T$ are plotted in FIG. 9B and typical tomograms are depicted in FIGS. 10A-D. The TWOI variation resembles the step-response of an under-damped harmonic oscillator with the time (horizontal) axis reversed [31]. A response of this kind is naturally expected as TC-PCT is analogous to a continuously tunable bandpass filter: the quality factor improves as the truncated-pulsewidth shortens and central or operating frequency decreases with the increase in delay [32].

TWOI is thus analogous to the filter output observed in the time domain after excitation. Output settling time for low frequencies would be longer than that for high frequencies for a given filter time constant. $d_{max}$ should be increased proportionally with $W_T$ to enable stable (steady or non-oscillatory) evaluation of TWOI. For the response in FIG. 9B, the stability is better than 98.5% if $W_T \leq 6$ ms. Here, stability refers to the constancy observed in the estimated value of TWOI over the interval 0-$W_T$ in the plot.

This leads to the conclusion that, for a given excitation chirp, the TWOI is independent of $W_T$ if $d_{max} \gg W_T$. In other words, the axial resolution should be made much higher than the depth-of-interest for the reliable estimation of this marker. For example, when reporting TWOI, the maximum delay should be significantly greater than the truncated pulse width, for example, at least 5 times, at least 10 times, or at least 20 times, the truncated pulse width. It will be understood that one skilled in the art can determine a suitable ratio of the maximum delay to the truncated pulse width, for a given material and a given set of system components and system configuration, by plotting the dependence of TWOI one of, or both of, truncated pulse width and maximum delay, and selecting a suitable range based on the stability of the TWOI values, in a manner similar to that illustrated in FIG. 9B.

The influence of excitation pulsewidth and pump intensity was also investigated and found that if the SNR remains unaltered, TWOI will be independent of these parameters as well. All these observations point towards the absolute nature of TWOI.

The TWOI was evaluated for a set of goat rib samples as a function of demineralization time (1, 2.5, 5, 10, 20, 30 and 40 hours in EDTA solution). Based on the fact that natural early mineral loss (osteoporosis) mainly occurs in the trabecular region [33], BVTs were constructed for ~1 mm thick trabecular region. TWOI was estimated for a volume of ~3×2×1 mm³ before (TWOI B) and after ($TWOI_A$) demineralization, and the fractional loss, ($TWOI_B$–$TWOI_A$)/$TWOI_B$×100, was calculated. Furthermore, µCT (Skyscan 1173, Bruker, USA) analysis was carried out to evaluate the BMD of these samples, intact and demineralized.

Figure 11:
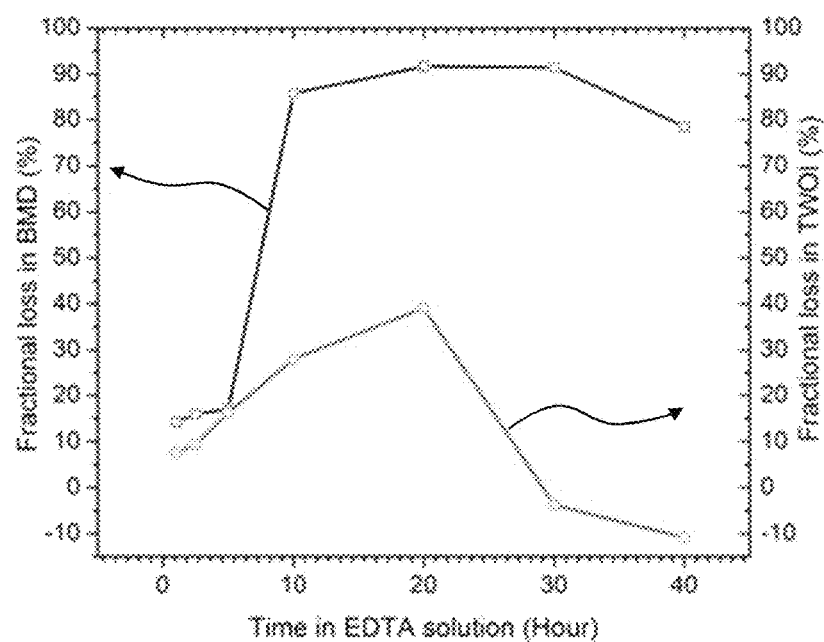
FIG. 11 plots the variation of fractional loss in μCT-estimated BMD and TWOI with demineralization-time for the goat rib sample (trabecular region), TC-PCT is ~5.6 times more sensitive than μCT at low demineralization levels.

FIG. 11 shows the variation of fractional loss in TWOI and BMD with demineralization time. BMD follows a monotonic response up to 30 hours of demineralization while for TWOI this behavior exists up to 20 hours. However, for low demineralization levels (up to 5 hours) that is likely to occur naturally in osteoporotic bones, the sensitivity of TWOI is ~5.6 times the BMD. The TC-PCT sensitivity to the changes in organic phase as well can be a reason for this advantage. For very high demineralization both the fractional losses undergo a reversal in direction. In the case of BMD this is due to a failure in the µCT procedure: the protocol defined for analyzing samples of mild demineralization did not converge for the 40-hour sample. Fractional loss in TWOI reverses sign for the 30- and 40-hour samples.

Limitations of traditional bone diagnostics/imaging techniques such as tissue ionizing disadvantage that forbids continuous monitoring, poor sensitivity and the impracticality to monitor disuse osteoporosis in space missions are the key motivators to search for alternate methods in this area. A related issue is the lack of sensitivity of traditional techniques to the biological conditions of bones resulting from changes in the organic phase. To address all these challenges together, the present efforts have been geared to demonstrate a photothermal 3D imaging modality featuring optical grade contrast for general skeletal diagnosis with the specific axial and lateral spatial resolution abilities for BMD monitoring and early mineral loss detection in micro-gravity environments as well as on Earth.

With TC-PCT, the irradiation energy is typically within the MPE ceiling and typical analysis duration is a few tens of seconds. It has the advantage of 3D tomographic reconstruction without the need for relative motion between the object and detector, which is the case with OCT or µCT. The depth-resolved imaging capability enables computational sectioning of cortical and trabecular regions for independent analysis, which is a remarkable feature also offered by µCT. Since the attenuation of thermal waves is stronger than that of X-rays in tissues, TC-PCT has a depth range limited to a few millimeters for excitation frequencies in the range 0.1-1 Hz. This range could be extended by using lower chirp frequencies, therefore slowing down the analysis with a compromise on the SNR and tissue dehydration. In a bone-tissue matrix, with 24 s long chirp, a depth range of 4 mm has been observed.

The potential of TC-PCT for depth selective imaging has found immediate application in the reconstruction of cortical and trabecular bone regions separately, and in the analysis of the relative influence of artificial demineralization in those regions. It is obvious from B1 and B2 of FIG. 8 that the modification to trabecular structure following very short demineralization time (0.5 hours) is marginal, yet this marginal modification is observable with TC-PCT (this is also the case for cortical layers). However, after 20-hour demineralization, there appear complex modifications to both cortical and trabecular regions and partial collapse of the trabecular network (as can be seen in A3 of FIG. 8). The TC-PCT volume appears expanded for both regions in this case. If this were true, then the corresponding TWOI would have remained larger than its intact value according to Eq. (13).

However, FIG. 11 reveals is that the TWOI keeps on decreasing with demineralization up to 20 hours. To address these contradictory results, the absolute PT amplitude was initially analyzed for the intact and demineralized conditions in a layer-by-layer manner taking the sum over every layer. It was found that the intact state has the highest PT amplitude and it decreases with the demineralization time up to 20 hours. This ensures the accuracy of the TWOI response in FIG. 11 and leaves questions on the image processing aspects of BVT. To further explore this issue, BVTs were generated for the intact, 0.5- and 20-hour samples using mean-threshold algorithm (another binarization technique) for the same surface-mesh parameter used for Huang method, E1-3 of FIG. 8. On comparing D3 and E3, one can see that the apparent cortical expansion in D3 is due to the inferior resolution of the Huang binarization algorithm, compared to mean-thresholding, for TC-PCT reconstruction. Although the mean-threshold algorithm offers better resolution, its noise immunity and sensitivity to demineralization are lower than Huang's. This discrepancy of apparent volume expansion was further examined by considering the absolute amplitude tomograms, F1-3 of FIG. 8. Here, the threshold was adjusted to improve the cortical contrast. The cortical thickness appears almost the same in all the three cases. Fortunately, the volume expansion or filling appears in the image only, not in the binary data, and it is assumed to be due to some artifacts at the surface-mesh generating stage: The algorithm first generates a set of 3-dimensional binarized data corresponding to the absolute amplitude TC-PCT. Using these data, with user defined mesh parameters, 3D surfaces are constructed to render volume visualization. For the successful reconstruction of a BVT the spatial separation between adjacent binary data should be greater than the resolution of the algorithm. For the 20-hour sample, the collapsed trabeculae become more closely packed due to bone volume compression so that their binary spatial separation in all directions falls below the algorithm resolution at many locations. Now, adjacent structures may get joined together to form a single object filling up the inter-data space, thus leading to an apparent volume expansion in the BVT. Since TWOI is calculated using the binary data, not the reconstructed volume, it remains unaffected by this discrepancy. However, the efficient use of TC-PCT for structural and functional imaging, and demineralization monitoring in bones demands optimum binarization algorithm and reconstruction protocols to be developed.

As per FIG. 11, the PT signal power keeps on decreasing with demineralization time up to 20 hours. The primary reason is the fall in the laser absorption and scattering coefficients with mineral loss [34]. As another reason there can be increase in the physical density of bone, in case, if the rate of mass loss is lower than that of volume compression. For 30- and 40-hour demineralization, the fractional loss in TWOI reverses sign indicating the post-demineralization signal amplitude is larger than the intact value. A possible reason is, following prolonged demineralization, excessive removal of bone material may enlarge the void fraction, especially within the trabecular region. The decreased geometric dimensions of the trabecular network will result in increased thermal confinement and higher thermal-wave amplitudes under similar optical absorption conditions. This effect can be amplified by the poor thermal conductivity of air: the increased void volume may have impeded the conductive loss rate, thereby sustaining a stronger thermal wave field within the trabecular pores. Also, the loss in mineral content may lead to a reduction in the physical density if the rate of mass loss is higher than that of volume loss. These physical mechanisms set an upper limit on the mineral loss that can be monitored by TC-PCT, however, this is not an impediment to clinical applications, as the physiological osteoporotic bone loss never reaches the demineralization level of B3 of FIG. 8. This hypothesis is further corroborated by the TWOI response, FIG. 11.

Figures 12A, 12B:
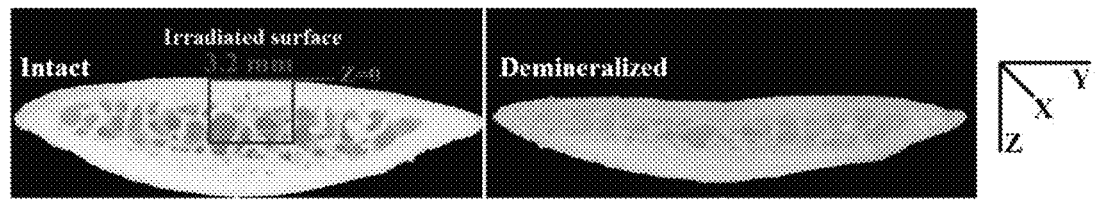
FIGS. 12A and 12B shows cross-sectional images of intact and demineralized goat rib samples.

Example 6: Truncated-Correlation Photothermal Coherence Tomography (TC-PCT) of Artificially Demineralized Animal Bones: 2- and 3-Dimensional Markers (MPA and TWOI) for Mineral-Loss Monitoring In order to formulate these morphometric protocols, TC-PCT results obtained for a goat rib sample (~5×1.6×0.42 cm$^3$) were employed. This specimen was prepared by keeping Canadian goat ribs immersed in water for about 3 weeks for complete decomposition of meat and blood. Clean ribs were rinsed with water and dried in sunlight. For artificial demineralization, the sample was dipped for 20 hours in ethylenediaminetetraacetic acid (EDTA) solution, which was prepared by diluting 0.5 M acid with equal volume of distilled water. Intact and demineralized samples are shown in cross section in FIGS. 12A and 12B.

Figure 12C:
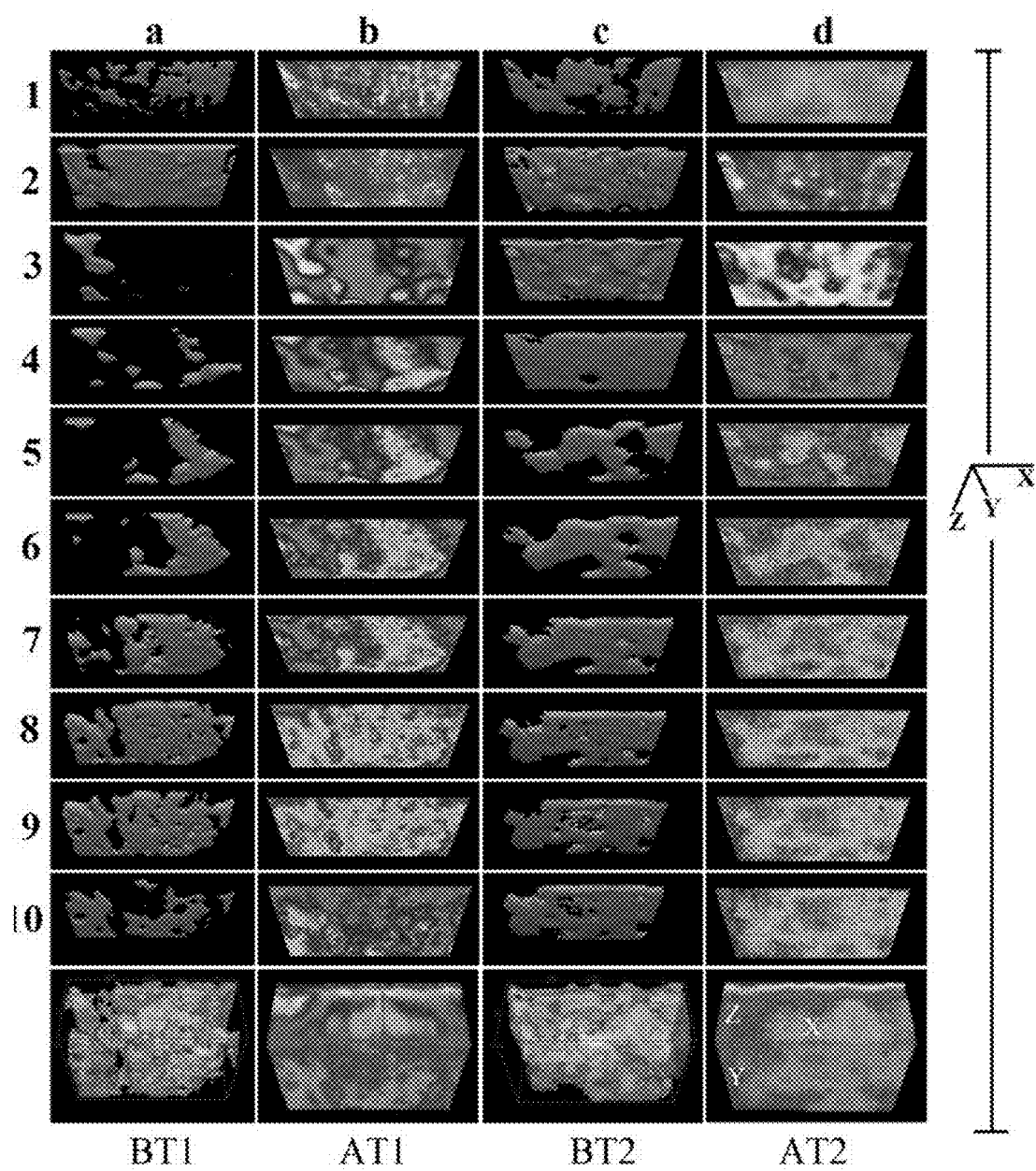
FIG. 12C shows a set of images based on performing TC-PCT measurements on the intact and demineralized samples shown in FIGS. 12A-B, where columns A and show binarized amplitude segments of the intact sample and demineralized sample, respectively, and columns B and D show layer-by-layer planar TC-PCT images of the intact sample and demineralized sample, respectively. The 10 binarized sequences, ~300 μm thick each, compose binarized amplitude tomograms BT1 and BT2. The 120 planar sequences, ~25 μm thick each, constitute the absolute amplitude tomograms AT1 and AT2.

FIG. 12C shows 2D amplitude images and 3D binarized stack sequences, both at different depths, as well as absolute amplitude and binarized full tomograms, all from the rib piece before and after demineralization. Images a1-10 and c1-10 are the binarized TC-PCT amplitude slices (~300 μm thick), vertically aligned as a function of depth (z-coordinate) below the irradiated surface, before and after demineralization, respectively. Each slice is formed by stacking and binarizing 12 depth-resolved planar images, each of thickness ~25 μm. b1-10 and d1-10 are the planar images sampled at every 12 ms delay interval, before and after demineralization, respectively. They depict the distribution of absolute TC-PCT amplitude in the specified plane. BT1 and BT2 are, respectively, the binarized amplitude tomogram for a depth of ~3 mm below the surface for the rib sample before and after demineralization. They are obtained by stacking a1-10 and c1-10, respectively. AT1 and AT2 are the corresponding absolute amplitude tomograms before and after demineralization, for the same depth. The imaged area is 4×3.2 mm$^2$. The experiment was done using the chirp-1 excitation with ~50-W peak power. Both truncated-reference pulsewidth and delay-step were 2 ms. Maximum delay applied was 120 ms, which corresponds to a depth of ~3 mm in bone.

The mean planar amplitude (MPA), a 2D parameter for a planar TC-PCT image to measure the photothermal strength of the layer is then defined, as follows. This parameter is evaluated as the ratio of the sum of TC-PCT amplitudes to the number of pixels, constituting a layer:

$$MPA = \frac{\sum_{i=1}^{n} S_i}{n} \qquad (14)$$

where, $S_i$ is the TC-PCT amplitude corresponding to the $i^{th}$ pixel and n is the number of pixels comprising the planar image.

To investigate the potential of this marker for monitoring the degree of demineralization four goat rib samples were considered, labeled RB10-13, demineralized in EDTA solution for 10, 20, 30 and 40 hours, respectively. They were subjected to chirp-1 TC-PCT analysis before and after demineralization. The results obtained for MPA before and after demineralization are shown in FIG. 13. A possible mechanism responsible for these MPA trends will be presented below.

FIG. 14 shows the variation of TWOI with the duration of demineralization for cortical and trabecular regions independently and together. Four ROIs (4×3.2 mm$^2$) were selected randomly on the sample surface for averaging. For individual analysis, the cortical and trabecular regions were reconstructed separately by suitably selecting the number of depth-resolved planar images, the ratio of sequences being determined by visually examining the onset of the trabecular signature.

In FIGS. 15A-C, binarized-amplitude tomograms of intact RB10 are shown, used for TWOI estimation, reconstructed individually and together from cortical and trabecular regions. The corresponding absolute TC-PCT amplitude tomograms are shown in FIGS. 15D-F. In FIG. 15A and FIG. 15D, z=0 corresponds to the irradiated cortical surface.

Figure 16A:
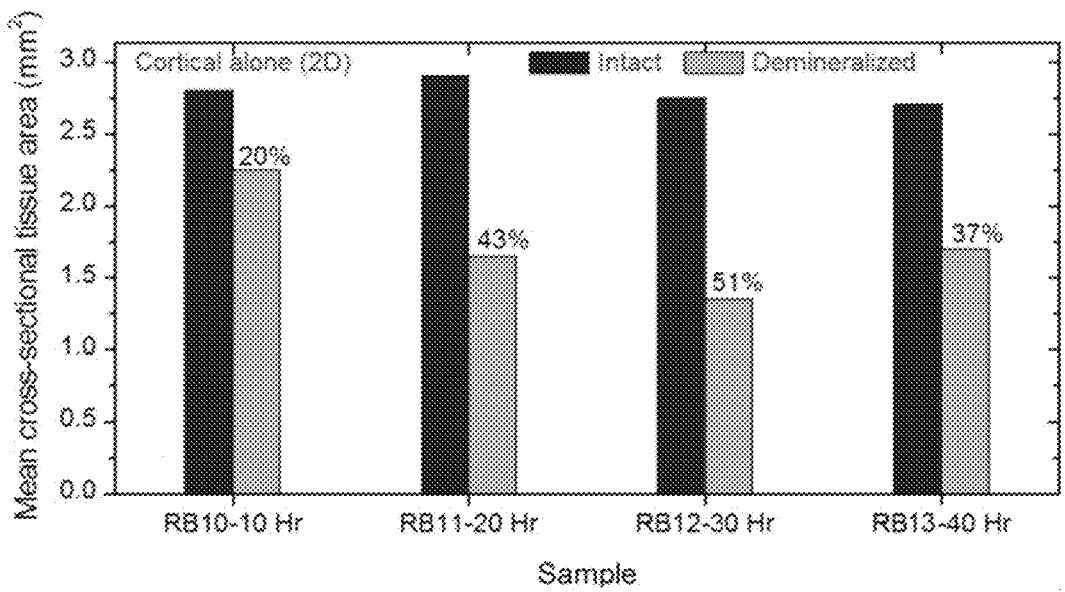
FIGS. 16A-F show various 2D and 3D μCT morphometric parameters estimated for the rib bones, RB10-13, before and after demineralization. These parameters were evaluated independently and together for the cortical and trabecular regions.

These samples were further analyzed using a μCT scanner (Skyscan 1173, Bruker, USA) over the same ROI, before and after demineralization. To establish clear distinctions between the merits and limitations of these complementary modalities (TC-PCT and μCT) for tracing demineralization, a comparative investigation was carried out over a broad range of mineral loss (up to 40 hours in EDTA) that is much larger than the natural range observed in osteoporotic cases. However, the interval was limited to 10 hours so as to fit the availability of μCT during this work. For this reason a comparison of the absolute sensitivity of the two methods was not carried out. A large set of 2- and 3-D X-ray morphometric parameters were estimated for cortical and trabecular regions separately and together as the reference markers for validating the TC-PCT results. In FIGS. 16A and B a pair of typical 2- and 3-D (TWOI) μCT parameters are depicted for individual and combined cortical and trabecular regions.

The prime criticism of X-ray based skeletal diagnostic techniques is their ionizing nature that forbids prolonged exposure for monitoring bone conditions, and their low sensitivity (contrast) for the early detection of mineral loss. Besides general clinical uses, a challenging area in which bone strength monitoring is of chief concern is the case of space flights under microgravity conditions as disuse osteoporosis puts astronauts at a higher risk of fracture on return to Earth [35]. In this situation, portable as well as non-ionizing methods suitable for continuous/frequent bone strength monitoring are desirable. Although techniques like MRTA and QUS are non-ionizing, their reliability and reproducibility are still in question, especially for early detection applications [36,37]. In this example, a hybrid-optical (photothermal) equivalent of μCT is demonstrated, with functionality comparable to that of OCT in terms of generation of large image sequences, and potential to trace the degree of mineral loss in artificially demineralized bones. Unlike μCT or Quantitative Ultrasound Tomography (QCT) the TC-PCT technique does not involve any relative motion (rotation) between target and detector. This is an advantage in view of portability. Regarding laser safety, the method is MPE compatible with typical analysis time limited to a few tens of seconds. Whereas X-ray modalities account for the back-projected photon absorption/attenuation profile in bones, TC-PCT depicts the distribution of optical and thermal parameters primarily (optical absorption coefficient and thermal diffusivity) within the sample. Owing to the strong attenuation of thermal waves, the depth range attainable with the current instrumentation is limited to ~4 mm in bone for a typical 0.1-0.5 Hz, 20-s long chirp. However, the probe-depth could be increased by using lower frequencies, consequently longer periods, which compromises imaging speed.

Since thermal-wave field properties are strongly thermal-diffusivity dependent which is a function of density, a measure of the volume occupied by the thermal-wave content should be indicative of the mineral density distribution within the bone sample. Based on this fact, for the morphometric analysis using TC-PCT, the 3D marker, TWOI, and its potential to track mineral loss in goat rib bones induced by low demineralization levels may be employed [38], as noted above. As a characteristic feature, it was observed that the TWOI response became anomalous above 20 hours of demineralization for goat rib samples continuously etched in EDTA solution of the specified concentration. μCT also possesses proven sensitivity for this kind of mild demineralization, usually for in-vitro diagnosis. The MPA marker measures the average PT activity of a TC-PCT layer mapped in terms of the absolute amplitude and is comparable with 2D μCT parameters like trabecular thickness and mean cross-sectional tissue area. A general trend observed in FIG. 13 for MPA is the progressive decrease as the depth below the surface increases. This is attributed to the attenuation of optical intensity with depth in the sample, due to absorption and scattering. In contrast to this steady behavior, there appears an anomalous response near the surface. One potential reason for this is the presence of peripheral contamination and its random reactions with EDTA. In addition, the temporal uncertainty in the camera frame trigger (~2 ms) is likely to cause a lapse in synchronizing the first frame with the start of the thermal relaxation. This may affect the surface/near-surface data contained in the early transient. Another possibility is the thermal confinement near the surface which tends to raise the mean temperature in the very near subsurface region.

In the following discussion, for the convenience of comparing the pre- and post-demineralization status of morphometric parameters, both TC-PCT and μCT, the percentile decrease in their value (δ(parameter)) due to EDTA treatment is considered. For the 10- and 20-hour demineralized samples there is an obvious drop in MPA following mineral loss. For 10-hour demineralization δ(MPA) is smaller (~38%) for the cortical region extending from ~0.3 to 1.2 mm (the surface slice data have been omitted because of their high uncertainty) compared to the trabecular region (~45%) extending from ~1.2 to 3 mm. Decrease in bone density (or BMD) is a natural consequence of demineralization. Any decrease in density (ρ) would increase bone thermal diffusivity ($\alpha = k/\rho c$, k and c being the thermal conductivity and specific heat capacity, respectively). Since diffusivity is a measure of the rate of heat flow/removal from the point of generation it would be reasonable to assume that the drop in the PT amplitude is a direct outcome of the decrease in BMD.

For the 20-hour demineralized sample, the average δ(MPA) for the predominantly cortical and trabecular regions are about 42% and 57%, respectively. The higher demineralization of the trabecular region compared to cortical layer is as expected due to its larger surface contact area with the EDTA solution. On moving to the 30-hour etched sample, the cortical MPA values before and after demineralization are comparable. For 40 hour demineralization the cortical δ(MPA) becomes partly slightly negative. A possible reason for this increase in cortical MPA is that excessive removal of bone material following prolonged demineralization may enlarge the void fraction within the cortical region and at the cortical-trabecular interface. Given the poor thermal conductivity of air (assuming the pores are air filled after drying the sample for imaging), the increased void volume may have impeded the conductive loss rate, thereby sustaining a stronger thermal-wave field within the cortical layer. In the case of 30-hour demineralization, the drop in PT signal strength due to the decrease in density has been possibly compensated by the reduced conductive loss rate. As in the case of 10 and 20 hours, the trabecular MPA after the 30-hour EDTA treatment is found to be lowered but only by ~25%. Here, too, the abovementioned air-pore contribution is assumed to be present. For 40-hour demineralization, MPA shows a slightly irregular response above and below the intact response curve, FIG. 13C, for the entire trabecular section. This anomalous behavior is due the extreme mineral loss that in turn leads to reasonable collapse of the trabecular structure.

In FIG. 16A, the dependence of mean cross-sectional tissue area (T.Ar), a typical 2D μCT morphometric parameter for the cortical region, on the demineralization time is presented. This marker measures the mean of the cross-sectional areas of all layers contained in a ROI, excluding air inclusions or pores [39,40]. There is a progressive increase in δ(T.Ar) with demineralization up to 30 hours; however, this fraction decreases for the 40-hour sample. For 10 and 20 hour demineralization both MPA and T.Ar follow the same trend. With demineralization no significant changes in MPA are noted for the 30-hour sample, while for 40 hours the post-demineralized sample exhibits slightly higher MPA values for the cortical layer.

Figure 16B:
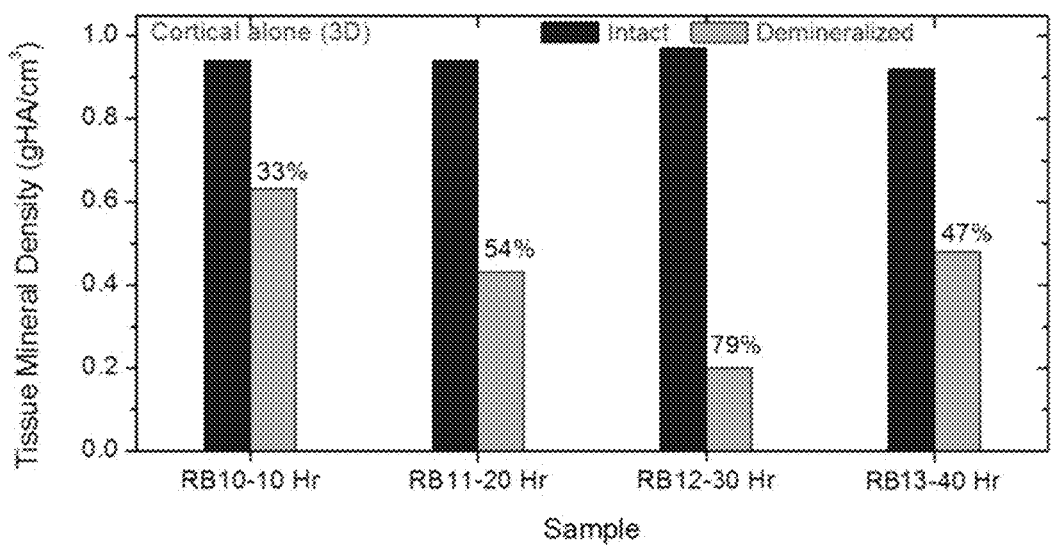
Figure 16C:
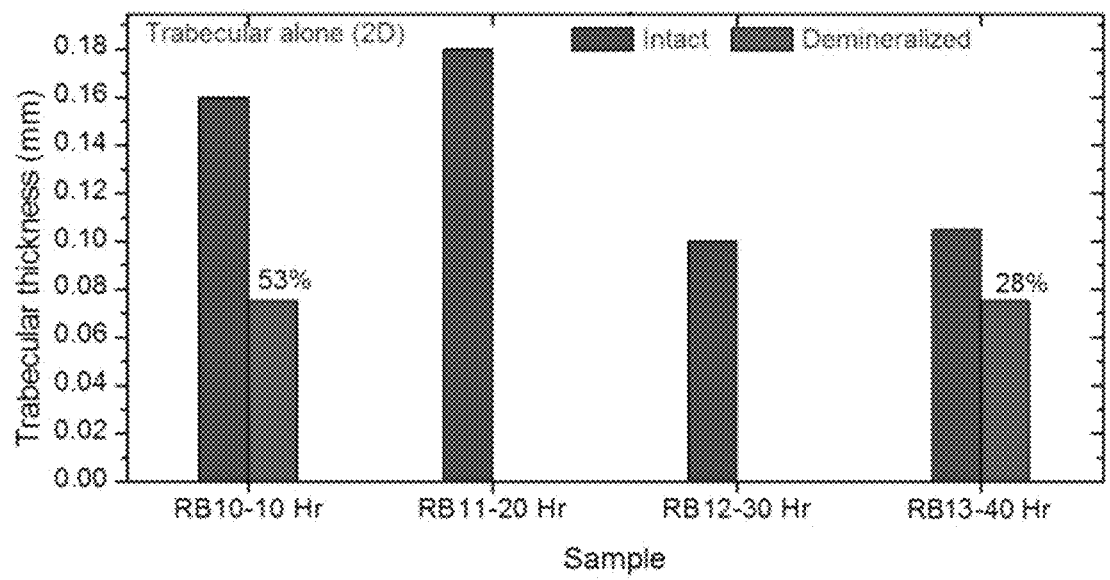
Figure 16D:
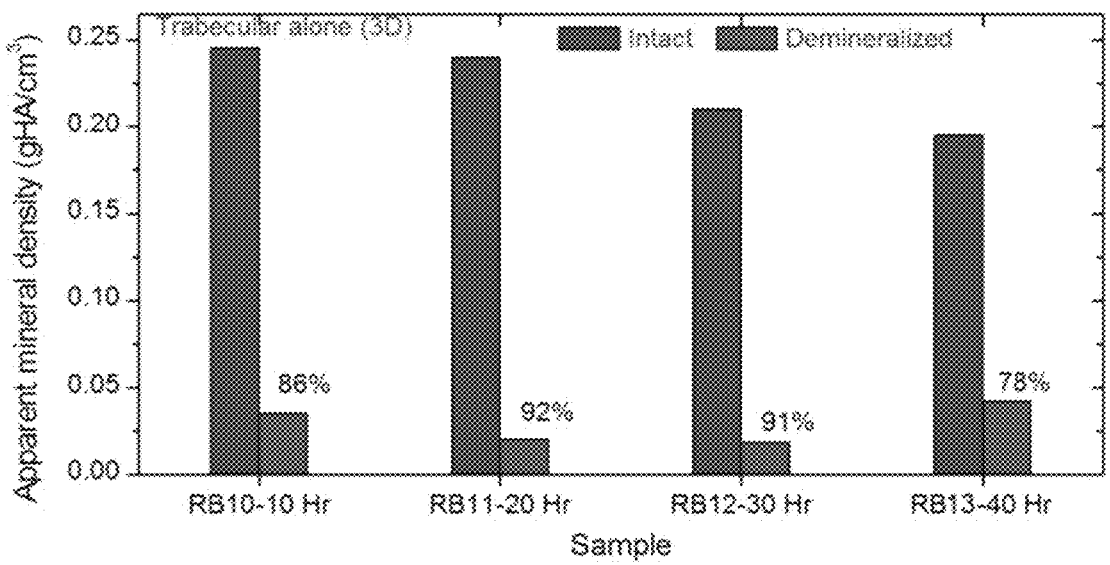
Figure 16E:
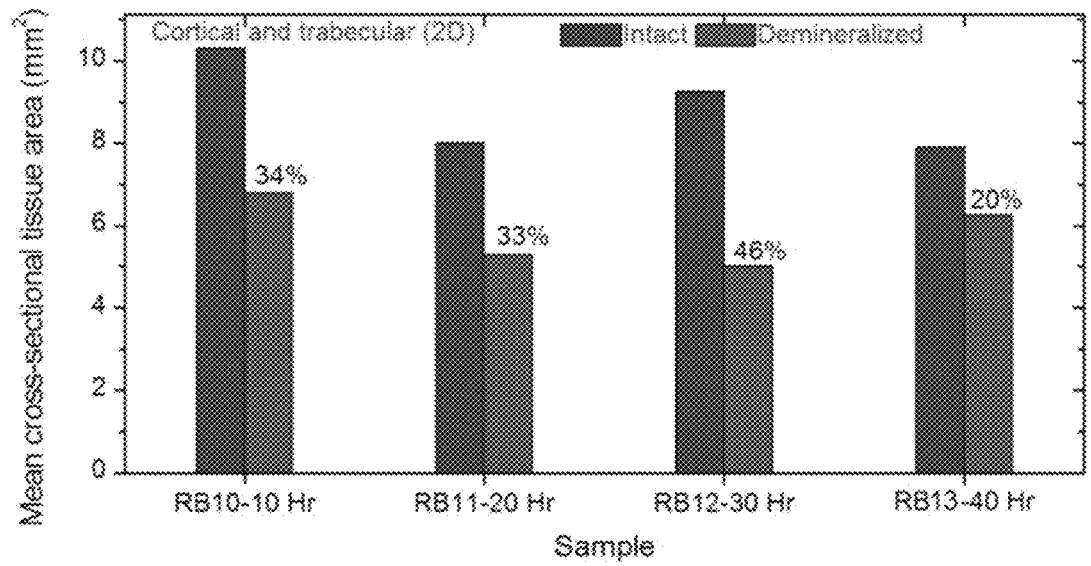
Figure 16F:
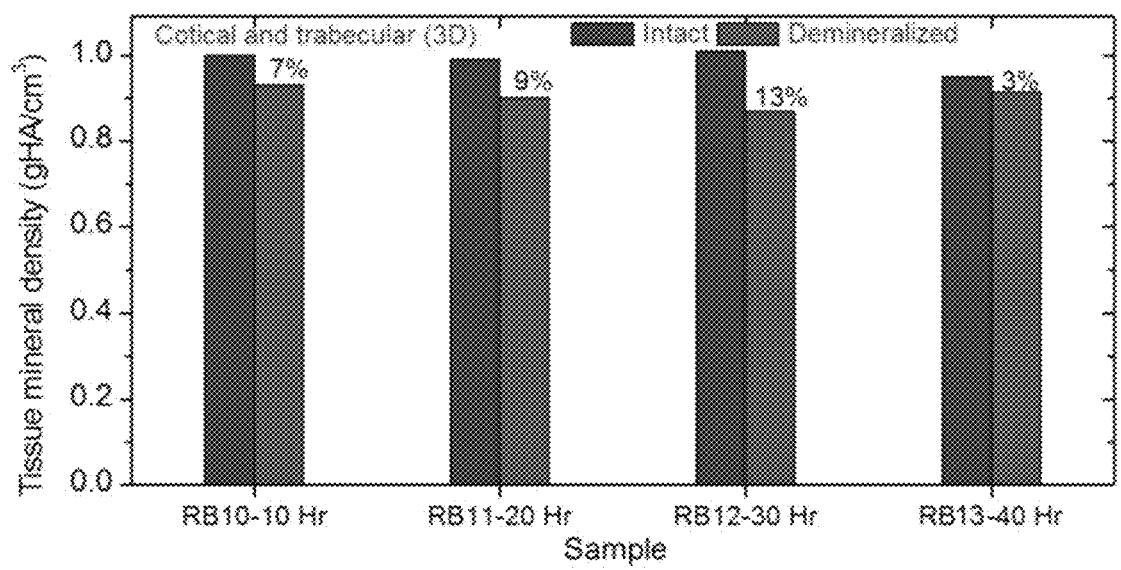

The variation of the μCT measured 2D trabecular thickness (Tb.Th), which is the volume weighted average of the local thickness assuming a structural model for the trabecular network is shown in FIG. 16C. The μCT protocol defined for the 10-hour sample failed in the case of 20- and 30-hour demineralization with partial success for 40 hours. So, no reliable conclusions could be made from the Tb.Th data. In the case of TC-PCT no such intermittent failures occurred for the trabecular MPA. For the combined cortical-trabecular analysis (FIG. 16E), there is no statistically meaningful difference in δ(Tb.Th) between 10- and 20-hour treatments. A reasonable decrease for 30-hour exposure and a reversal after 40 hours are similar to those trends observed for the purely cortical region.

Figures 14A, 14B, 14C:
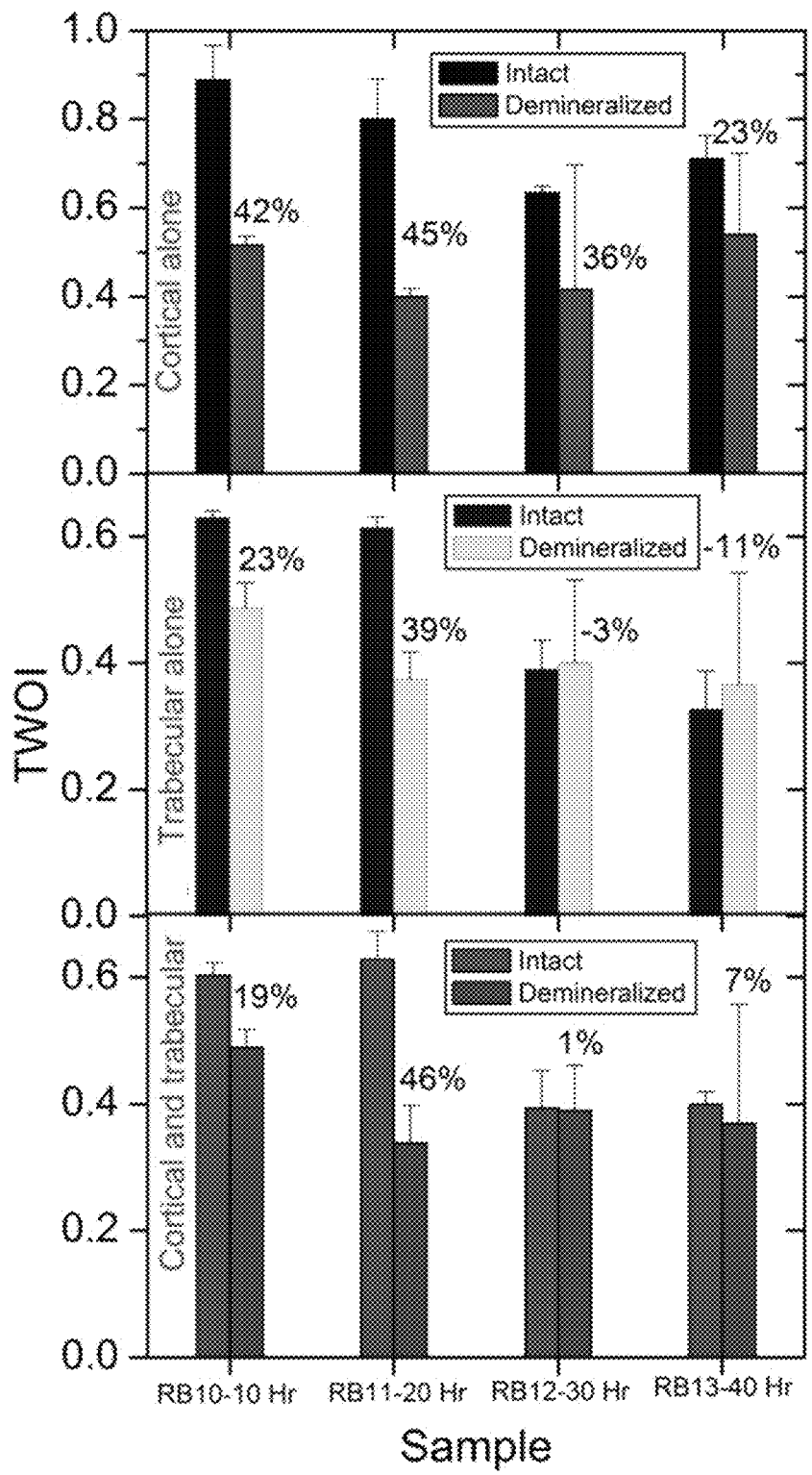
FIGS. 14A-C plot the variation of TWOI with duration of demineralization estimated individually (A, B) and together (C) for the cortical and trabecular regions.

As seen in FIG. 14A, the 3D TC-PCT marker, TWOI, yields a marginally increasing δ value between 10 and 20 hours. For 30 hours the trend is toward a decrease but with high uncertainty, which is true for 40 hours as well. A related μCT parameter, the tissue mineral density (Tb.v.TMD), follows a progressively increasing δ up to 30 hours, then a decrease, FIG. 16B Up to 20 hours, both TWOI and Tb.v.TMD follow the same trend qualitatively for the cortical region. For purely trabecular and cortical-trabecular combination similar responses are observed for TWOI (FIG. 14 and c). The μCT markers are consistent with this behavior for the same regions, except for the discrepancy in Tb.Th for 20 and 30-hour etched trabecular portion, FIG. 16C. Here, the absence of data for the post-demineralized samples is due to a μCT protocol failure. A decrease in δ is a common feature followed by both μCT and TC-PCT parameters for times between 30 and 40 hours, i.e., for very high mineral loss. In general the TC-PCT markers, both MPA and TWOI, unambiguously trace the extent of mineral loss up to 20 hours. This has already been verified for a sample continuously demineralized at 30 min intervals [38]. The μCT markers are monotonically sensitive up to 30 hours in most cases.

Figures 17A, 17B, 17C:
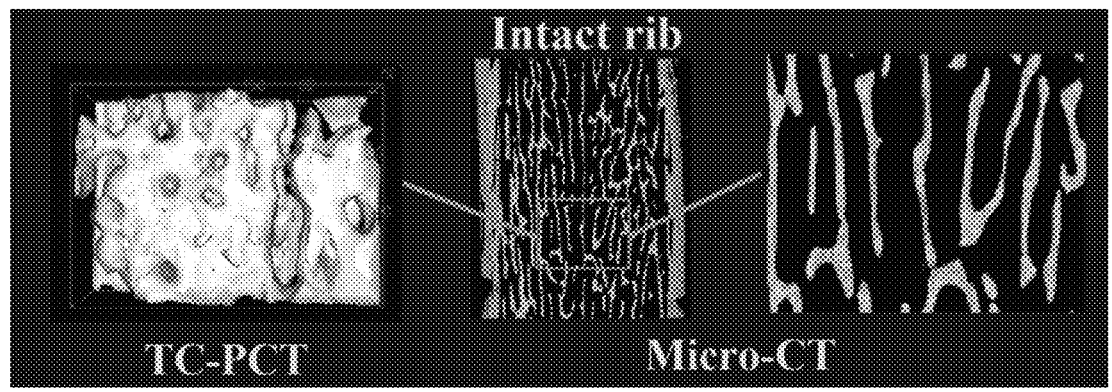
FIGS. 17A-F present binarized amplitude TC-PCT and μCT images of the goat rib sample before and after demineralization. The μCT images of the whole sample (~3.8 cm long) are shown in FIGS. 17B and 17E. The ROI for TC-PCT (4×3.2 mm$^2$) is outlined in green color. The TC-PCT image and zoomed-in version of μCT image corresponding to the ROI are shown in the left (FIGS. 17A and 17D) and right (FIGS. 17C and 17F) columns, respectively.
Figures 17D, 17E, 17F:
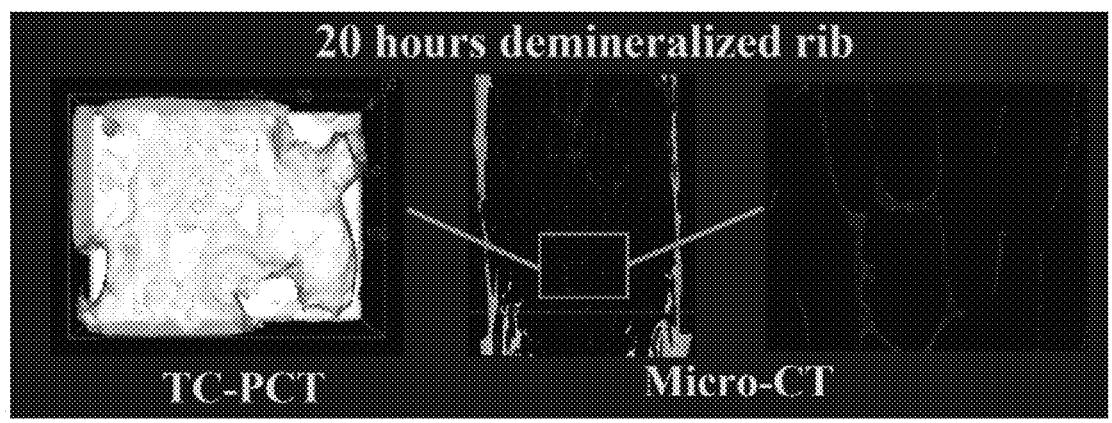

A major μCT disadvantage is the lack of convergence of measurement protocols in certain cases due to the system dynamic range limitations, as seen in FIG. 16C. Here a null-result was obtained for 20 and 30 hour demineralized samples for the protocol defined for 10-hour demineralization. The dynamic range features of both these modalities are further investigated by analyzing the binarized amplitude TC-PCT and μCT image of the 20-hour treated rib before and after demineralization (FIG. 17). The tomogram is a view from below, from the trabecular surface towards the cortical layer. It can be seen that TC-PCT offers much better dynamic range which allows the trabecular structure of the demineralized sample to be clearly visible along with the cortical portion, justifying the previous argument.

X-ray based methods measure the absorption/attenuation of photons (mostly) by the mineral content in bones and tomographic reconstruction is done using back-projected planar images. Since scattering and diffraction effects are negligible for bone X-rays, a well-defined structural imaging is possible. In the case of TC-PCT depth coded planar images primarily depict the (photo)thermal wave distribution associated with optical absorbers. Not only the absorber distribution, but also the spatial variation of thermophysical parameters (for example, density, effusivity, etc.) influences the thermal wave distribution within and around an object. This means that the TC-PCT generates a functional image of the thermooptical features of the sample. If the separation between adjacent objects (say, trabeculae) is large enough to be axially depth-resolved locally without overlapping thermal-wave contributions from other depths, then structural imaging is possible with TC-PCT on a spatial resolution scale of the thermal wavelength. Since the thermal diffusion length is inversely correlated with the square root of frequency, higher resolution for improved structural imaging would be possible at higher frequencies that demand shorter excitation pulsewidth. However, this will limit the depth range. With chirp-1 excitation the lateral resolution observed in bone is ~100 μm.

Example 7: Application of TC-PCT in Burn Depth Assessment

Three dimensional imaging of soft tissues, a case of broad biomedical interest, is yet another area where TC-PCT can deliver sharp images of the topography and crisp photothermal features of distributed optical absorbers. Burn-depth estimation is a typical example where a quick, non-invasive and non-contacting assessment of the depth of a wound is a priority for efficient healing [41-44]. It is well known that heat treatment considerably alters the optical and thermal properties of tissues [45]. The usefulness of the present tomographic modality for burn-depth assessment has been evaluated using a pig ear sample (~3.0×3.0×0.8 $cm^3$). By means of a copper strip (~2×2 $mm^2$ contact area) maintained at ~150° C. through resistive heating, two burns were created on the surface (FIG. 18A). Heating duration was 5 s for burn W1 and 10 s for burn W2. The imaged area was ~20×16 $mm^2$. Amplitude tomograms were generated with chirp-1 waveform excitation (FIGS. 18B-D). Burn injuries extending down to a depth of about 2.5 mm are observable. It has been verified that TC-PCT resolves tissue ablation much deeper than can be observed in the pure optical image shown in FIG. 18E. A higher resolution tomogram has been recorded for another burn (W3) on a different pig ear sample (FIGS. 18F-J). W3 was made with a 2×1 mm hot tip at 150° C. by making contact for 3 s. An area of 4.0×3.2 $mm^2$ was imaged. It is noticed that the superficial-dermal/deep-dermal burn appears slightly broadened in the TC-PCT image (FIGS. 18H, 18I) owing to its high contrast compared to the surface picture (FIG. 18J).

Example 8: Intensity/BMD-Scaled Bone Tomography

A unique characteristic of absolute amplitude TC-PCT is the feasibility of intensity scaling by which the tomogram can be modified to show the regions of a specific band of PT amplitudes. Since the PT signal amplitude is directly correlated to the BMD, this feature turns out to be a means for the selective mapping of regions of a specific BMD range. This possibility has been examined using a mouse femur (FIG. 19). The illuminated cortical surface was the plane of imaging (BF). The sequential two-dimensional images are stacked, without binary conversion, to form the amplitude tomogram, TF. Images TR1-5 are the rear views of the amplitude tomogram TF for different amplitude thresholds: 0, 20, 40, 60 and 80% of the maximum amplitude, respectively. BR is the corresponding rear view photograph. Threshold selection enables the blocking of PT sources below it from contributing to the image. As the threshold approaches 60% of the maximum signal only the hard cortical portions appear in the image (TR4). The bluish background is due to the ambient IR signal.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. Bell, A. G. On the production and reproduction of sound by light. *Am. J. Sci.* 20, 305-324 (1880).
2. Bell, A. G. Upon the production of sound by radiant energy. *Phil. Mag.* 11, 510-528 (1881).
3. Lord Rayleigh. The Photophone. *Nature* 23, 274-275 (1881).
4. Rosencwaig, A. *Photoacoustics and Photoacoustic Spectroscopy* (John Wiley, New Jersey, 1980).
5. Almond, D. P. & Patel, P. M. *Photothermal Science and Techniques* (Chapman and Hall, London, 1996).
6. Mandelis, A. Diffusion waves and their uses. *Phys. Today* 53, 29-33 (2000).
7. Bialkowski, S. E. *Photothermal Spectroscopy Methods for Chemical Analysis* (Wiley-Interscience, New York, 1995).
8. Mandelis, A., Nicolaides, L. & Chen, Y. Structure and the reflectionless/refractionless nature of parabolic diffusion-wave fields. *Phys. Rev. Lett.* 87, 020801 (2001).
9. Kirkbright, G. F. & Miller, R. M. Cross-correlation techniques for signal recovery in thermal wave imaging. *Anal. Chem.* 55, 502-506 (1983).
10. Mandelis, A. Frequency modulated (FM) time delay photoacoustic and photothermal wave spectroscopies. Technique, instrumentation, and detection. Part I: Theoretical. *Rev. Sci. Instrum.* 57, 617-621 (1986).
11. Tabatabaei, N. & Mandelis, A. Thermal coherence tomography using match filter binary phase coded diffusion waves. *Phys. Rev. Lett.* 107, 165901 (2011).
12. Levanon, N. & Mozeson, E. *Radar Signals* (John Wiley & Sons Inc., New Jersey, 2004).
13. Kaiplavil, S. & Mandelis, A. Highly depth-resolved chirped pulse photothermal radar for bone diagnostics. *Rev. Sci. Instrum.* 82, 074906 (2011).
14. American National Standard for Safe Use of Lasers. ANSI Z136.1 (2007).
15. Breitenstein, O. & Langenkamp, M. *Lock-In Thermography: Basics and Use for Functional Diagnostics of Electronic Components* (Springer-Verlag, Heidelberg, 2003).
16. Gaiduk, A., Yorulmaz, M., Ruijgrok, P. V., & Orrit, M. Room-temperature detection of a single molecule's absorption by photothermal contrast. *Science* 330, 353-356 (2010).
17. Tabatabaei, N., Mandelis, A. & Amaechi, B. T. Thermophotonic radar imaging: An emissivity-normalized modality with advantages over phase lock-in thermography. *Appl. Phys. Lett.* 98, 163706 (2011).
18. White, T. D. & Folkens, P. A. *The Human Bone Manual* (Elsevier Academic Press, California, 2005).
19. Rosencwaig, A. & Gersho, A. Theory of the photoacoustic effect with solids. *J. Appl. Phys.* 47, 64-69 (1976).
20. Vollmer, M. & Mollmann, K. P. *Infrared Thermal Imaging* (Wiley-VCH GmbH & Co., Weinheim, 2010).
21. Malvino, A. P. & Leach, D. P. *Digital Principles and Applications* (McGraw-Hill, New York, 1994).
22. Romer, A. S. & Parsons, T. S. *The Vertebrate Body* (Saunders College Pub., Philadelphia, 1986).
23. http://rsb.info.nih.gov/ij/
24. L. Huang and M. J. Wang, "Image thresholding by minimizing the measures of fuzziness", Pattern Recogn. 28, 41-51 (1995).
25. K. N. Plataniotis and A. N. Venetsanopoulos, *Color Image Processing and Applications* (Springer-Verlag, 2000).
26. A. Takeuchi, R. Araki, S. G. Proskurin, Y. Takahashi, Y. Yamada, J. Ishii, S. Katayama and A. Itabashi, "A new method of bone tissue measurement based upon light scattering", *J. Bone. Miner. Res.* 12, 261-266 (1997).
27. Bartl, R & Frisch, B. *Osteoporosis: Diagnosis, Prevention, Therapy* (Springer-Verlag, Berlin, 2009).
28. Callis, G. & Sterchi, D. Decalcification of bone: Literature review and practical study of various decalcifying agents, methods, and their effect on bone histology. *J. Histotechnology* 21, 49-58 (1998).
29. Ehrlicha, H., Koutsoukos, P. G., Demadis, K. D. & Pokrovsky, O. S. Principles of demineralization: Modern strategies for the isolation of organic frameworks, Part II. Decalcification. *Micron* 40, 169-193 (2009).
30. Hoffmeister, B. K., Whitten, S. A., Kaste, S. C. & Rho, J. Y. Effect of collagen and mineral content on the high-frequency ultrasonic properties of human cancellous bone. *Osteoporos Int* 13, 26-32 (2002).
31. B. C. Kuo and F. Golnaraghi, *Automatic Control Systems* (Wiley, 2002).
32. S. Kaiplavil and A. Mandelis, "Truncated-correlation photothermal coherence tomography for deep subsurface analysis", Nature Photonics DOI: 10.10.1038/NPHOTON.2014.111 (1-8) (Jun. 29, 2014).
33. L. Bonnick, *Bone Densitometry in Clinical Practice: Application and Interpretation* (Humana Press, 2010).
34. N. Ugryumova, S. J. Matcher and D. P. Attenburrow, "Measurement of bone mineral density via light scattering", Phys. Med. Biol. 49, 469-483 (2004).
35. L. Vico, P. Collet, A. Guignandon, M. H. Lafage-Proust, T. Thomas, M. Rehaillia and C. Alexandre, "Effects of long-term microgravity exposure on cancellous and cortical weight-bearing bones of cosmonauts," *Lancet* 355, 1607-1611 (2000).
36. S. Nayak, I. Olkin, H. Liu, M. Grabe, M. K. Gould, I. E. Allen, D. K. Owens and D. M. Bravata, "Meta-analysis: Accuracy of ultrasound for identifying patients with osteoporosis," *Ann. Intern. Med.* 144, 832-841 (2006).
37. C. R. Steele, L. J. Zhou, D. Guido, R. Marcus, W. L. Heinrichs and C. Cheema, "Noninvasive determination of ulnar stiffness from mechanical response—in vivo comparison of stiffness and bone mineral content in humans," *J. Biomech. Eng.* 110, 87-96 (1988).
38. S. Kaiplavil, A. Mandelis, X. D. Wang, and T. Feng, "Photothermal tomography for the functional and structural evaluation and early mineral loss monitoring in bones", Biomedical Optics Express 5 (8), 2488-2502 (2014) [DOI:10.1364/BOE.5.002488].
39. S. L. Bonnick, *Bone Densitometry in Clinical Practice: Application and Interpretation*, Humana Press, New York (2010).
40. A. M. Parfitt, M. K. Drezner, F. H. Glorieux and J. A. Kanis, "Bone histomorphometry: standardization of nomenclature, symbols, and units," *J. Bone Miner. Res.* 2, 595-610 (1987).
41. Herndon, D. N. *Total Burn Care* (Elsevier Inc., New York, 2007).
42. Monstrey, S., Hoeksema, H., Verbelen, J., Pirayesh, A. & Blondeel, P. Assessment of burn depth and burn wound healing potential. *Burns* 34, 761-769 (2008).
43. Jaskille, A. D., Shupp, J. W., Jordan, M. H. & Jeng, J. C. Critical review of burn depth assessment techniques: Part I. Historical review. *J. Burn Care Res.* 30, 937-947 (2009).
44. Jaskille, A. D., Shupp, J. W., Jordan, M. H. & Jeng, J. C. Critical review of burn depth assessment techniques: Part II. Review of laser Doppler technology. *J. Burn Care Res.* 31, 151-157 (2010).
45. Welch, A. J. & van Gemert, M. J. C. (Eds.). *Optical-Thermal Response of Laser-Irradiated Tissue* (Plenum, New York, 1995).

Therefore what is claimed is:

1. A method of performing photothermal imaging, the method comprising:
   generating an excitation chirped waveform comprising a chirped sequence of pulses;
   controlling a laser according to the excitation chirped waveform, such that the laser emits a chirped sequence of laser pulses;
   directing the chirped sequence of laser pulses onto a sample;
   detecting, with an infrared camera, photothermal radiation emitted from the sample, thereby obtaining time-dependent photothermal signal data for each image pixel of the infrared camera;
   generating a truncated chirped waveform comprising a chirped sequence of truncated pulses, wherein each truncated pulse has a pulsewidth less than that of the pulses of the excitation chirped waveform, and wherein each truncated pulse is delayed by a pre-selected time delay relative to a corresponding pulse of the chirped sequence of pulses;
   cross-correlating the time-dependent photothermal signal data with the truncated chirped waveform, thereby obtaining, for each pixel of the infrared camera, time-dependent cross-correlation data; and
   generating image data based on the time-dependent cross-correlation data.

2. The method of claim 1 wherein the chirped sequence of pulses comprises pulses having a fixed pulse width and a chirped pulse repetition rate.

3. The method of claim 2 wherein the cross correlation is performed based on in-phase and quadrature representations of the time-dependent photothermal signal data.

4. The method of claim 2 wherein the image data is generated by:
   calculating, for each pixel, a time-dependent amplitude from the time-dependent cross-correlation data;
   identifying, for each pixel, the peak of the time-dependent amplitude; and
   calculating, for each pixel, a measure associated with the peak of the time-dependent amplitude.

5. The method of claim 4 wherein the measure comprises one or more of peak amplitude, phase value associated with the peak amplitude, or time value associated with the peak amplitude.

6. The method of claim 1 further comprising:
   cross-correlating the time-dependent photothermal signal data with one or more additional truncated chirped waveforms and generating additional image data; and
   generating volumetric image data based on the image data and the additional image data.

7. The method of claim 6 wherein the volumetric image data is a binarized volumetric image data.

8. The method of claim 6 further comprising processing the volumetric image data to calculate an occupation index within a spatial region, wherein the occupation index is calculated based on the ratio of the volume of binarized thermal wave field divided by the volume of the spatial region.

9. The method of claim 1 further comprising processing the image data to calculate a mean planar amplitude for a set of image pixels, wherein the mean planar amplitude is calculated by dividing the sum of the amplitude values associated with each pixel of the set of image pixels by the number of image pixels within the set of image pixels.

10. A system for performing photothermal imaging, the system comprising:
    a laser;
    an infrared camera; and
    computer hardware including processor electronics configured to perform operations comprising:
       generating an excitation chirped waveform comprising a chirped sequence of pulses;
       controlling the laser according to the excitation chirped waveform, such that the laser emits a chirped sequence of laser pulses onto a sample;
       detecting, with the infrared camera, photothermal radiation responsively emitted from the sample, thereby obtaining time-dependent photothermal signal data for each image pixel of the infrared camera;
       generating a truncated chirped waveform comprising a chirped sequence of truncated pulses, wherein each truncated pulse has a pulsewidth less than that of the pulses of the excitation chirped waveform, and wherein each truncated pulse is delayed by a pre-selected time delay relative to a corresponding pulse of the chirped sequence of pulses;
       cross-correlating the time-dependent photothermal signal data with the truncated chirped waveform, thereby obtaining, for each pixel of the infrared camera, time-dependent cross-correlation data; and
       generating image data based on the time-dependent cross-correlation data.

11. A method of performing acousto-thermal imaging, the method comprising:
    generating an excitation chirped waveform comprising a chirped sequence of pulses;
    controlling a high-frequency ultrasound source according to the excitation chirped waveform, such that the high-frequency ultrasound source emits a chirped sequence of ultrasound pulses;
    directing the chirped sequence of ultrasound pulses onto a sample;

detecting, with an infrared camera, photothermal radiation emitted from the sample, thereby obtaining time-dependent photothermal signal data for each image pixel of the infrared camera;

generating a truncated chirped waveform comprising a chirped sequence of truncated pulses, wherein each truncated pulse has a pulsewidth less than that of the pulses of the excitation chirped waveform, and wherein each truncated pulse is delayed by a pre-selected time delay relative to a corresponding pulse of the chirped sequence of pulses;

cross-correlating the time-dependent photothermal signal data with the truncated chirped waveform, thereby obtaining, for each pixel of the infrared camera, time-dependent cross-correlation data; and generating image data based on the time-dependent cross-correlation data.

12. The method of claim 11 wherein the chirped sequence of pulses comprises pulses having a fixed pulse width and a chirped pulse repetition rate.

13. The method of claim 12 wherein the cross correlation is performed based on in-phase and quadrature representations of the time-dependent photothermal signal data.

14. The method of claim 12 wherein the image data is generated by:
calculating, for each pixel, a time-dependent amplitude from the time-dependent cross-correlation data;
identifying, for each pixel, the peak of the time-dependent amplitude; and
calculating, for each pixel, a measure associated with the peak of the time-dependent amplitude.

15. A system for performing acousto-thermal imaging, the system comprising:
a high-frequency ultrasound source;
an infrared camera; and
computer hardware including processor electronics configured to perform operations comprising:
generating an excitation chirped waveform comprising a chirped sequence of pulses;
controlling the high-frequency ultrasound source according to the excitation chirped waveform, such that the high-frequency ultrasound source emits a chirped sequence of ultrasound pulses onto a sample;
detecting, with the infrared camera, photothermal radiation responsively emitted from the sample, thereby obtaining time-dependent photothermal signal data for each image pixel of the infrared camera;
generating a truncated chirped waveform comprising a chirped sequence of truncated pulses, wherein each truncated pulse has a pulsewidth less than that of the pulses of the excitation chirped waveform, and wherein each truncated pulse is delayed by a pre-selected time delay relative to a corresponding pulse of the chirped sequence of pulses;
cross-correlating the time-dependent photothermal signal data with the truncated chirped waveform, thereby obtaining, for each pixel of the infrared camera, time-dependent cross-correlation data; and
generating image data based on the time-dependent cross-correlation data.

16. A method of performing photo-acoustic imaging, the method comprising:

generating an excitation chirped waveform comprising a chirped sequence of pulses;

controlling a laser according to the excitation chirped waveform, such that the laser emits a chirped sequence of laser pulses;

directing the chirped sequence of laser pulses onto a sample;

detecting, with an ultrasound array, ultrasound waves emitted from the sample and beamforming the received ultrasound signals to obtain spatially-resolved time-dependent ultrasound signal data from the sample;

generating a truncated chirped waveform comprising a chirped sequence of truncated pulses, wherein each truncated pulse has a pulsewidth less than that of the pulses of the excitation chirped waveform, and wherein each truncated pulse is delayed by a pre-selected time delay relative to a corresponding pulse of the chirped sequence of pulses;

cross-correlating the spatially resolved time-dependent ultrasound signal data with the truncated chirped waveform, thereby obtaining time-dependent cross-correlation data; and generating image data based on the time-dependent cross-correlation data.

17. The method of claim 16 wherein the chirped sequence of pulses comprises pulses having a fixed pulse width and a chirped pulse repetition rate.

18. The method of claim 16 wherein the cross correlation is performed based on in-phase and quadrature representations of spatially-resolved time-dependent ultrasound signal data.

19. A system for performing photo-acoustic imaging, the system comprising:
a laser;
an ultrasound array; and
computer hardware including processor electronics configured to perform operations comprising:
generating an excitation chirped waveform comprising a chirped sequence of pulses;
controlling the laser according to the excitation chirped waveform, such that the laser emits a chirped sequence of laser pulses onto a sample;
detecting, with an ultrasound array, ultrasound waves responsively emitted from the sample and beamforming the received ultrasound signals to obtain spatially-resolved time-dependent ultrasound signal data from the sample;
generating a truncated chirped waveform comprising a chirped sequence of truncated pulses, wherein each truncated pulse has a pulsewidth less than that of the pulses of the excitation chirped waveform, and wherein each truncated pulse is delayed by a pre-selected time delay relative to a corresponding pulse of the chirped sequence of pulses;
cross-correlating the spatially resolved time-dependent ultrasound signal data with the truncated chirped waveform, thereby obtaining time-dependent cross-correlation data; and
generating image data based on the time-dependent cross-correlation data.

* * * * *